(12) United States Patent
Zysman-Colman et al.

(10) Patent No.: US 10,388,888 B2
(45) Date of Patent: Aug. 20, 2019

(54) LIGHT EMITTING ELECTROCHEMICAL CELLS AND COMPOUNDS

(71) Applicant: UNIVERSITY COURT OF THE UNIVERSITY OF ST ANDREWS, St Andrews (GB)

(72) Inventors: Eli Zysman-Colman, Fife (GB); Michael Yin Wong, Fife (GB)

(73) Assignee: UNIVERSITY COURT OF THE UNIVERSITY OF ST ANDREWS, St Andrews (GB)

( * ) Notice: Subject to any disclaimer, the term of this patent is extended or adjusted under 35 U.S.C. 154(b) by 0 days.

(21) Appl. No.: 15/540,612

(22) PCT Filed: Dec. 29, 2015

(86) PCT No.: PCT/GB2015/054172
§ 371 (c)(1),
(2) Date: Jun. 29, 2017

(87) PCT Pub. No.: WO2016/108046
PCT Pub. Date: Jul. 7, 2016

(65) Prior Publication Data
US 2017/0352818 A1 Dec. 7, 2017
US 2019/0214576 A9 Jul. 11, 2019

(30) Foreign Application Priority Data

Dec. 29, 2014 (GB) .................................. 1423289.6
Apr. 29, 2015 (GB) .................................. 1507337.2

(51) Int. Cl.
| | | |
|---|---|---|
| *C07D 209/86* | (2006.01) | |
| *H01L 51/00* | (2006.01) | |
| *H01L 51/50* | (2006.01) | |
| *C07C 211/06* | (2006.01) | |
| *C07D 233/61* | (2006.01) | |
| *C07D 403/14* | (2006.01) | |
| *C09K 11/06* | (2006.01) | |

(52) U.S. Cl.
CPC ........ *H01L 51/0072* (2013.01); *C07C 211/06* (2013.01); *C07D 209/86* (2013.01); *C07D 233/61* (2013.01); *C07D 403/14* (2013.01); *C09K 11/06* (2013.01); *H01L 51/0061* (2013.01); *H01L 51/5032* (2013.01); *C09K 2211/1007* (2013.01); *C09K 2211/1014* (2013.01); *C09K 2211/1018* (2013.01); *C09K 2211/1029* (2013.01); *C09K 2211/1044* (2013.01); *H01L 51/0051* (2013.01); *H01L 51/0059* (2013.01); *H01L 51/0067* (2013.01); *H01L 51/5012* (2013.01)

(58) Field of Classification Search
CPC .............. C07D 209/86; H01L 51/0067
See application file for complete search history.

(56) References Cited

U.S. PATENT DOCUMENTS

| | | |
|---|---|---|
| 8,643,268 B2 | 2/2014 | Ogiwara et al. |
| 8,847,218 B2 | 9/2014 | Nishimura et al. |
| 8,993,129 B2 | 3/2015 | Endo et al. |
| 9,153,788 B2 | 10/2015 | Adachi et al. |
| 9,219,242 B2 | 12/2015 | Ogiwara et al. |
| 9,502,668 B2 | 11/2016 | Adachi et al. |
| 9,660,199 B2 | 5/2017 | Shizu et al. |
| 2012/0241732 A1 | 9/2012 | Endo et al. |
| 2013/0306945 A1 | 11/2013 | Seo |
| 2014/0103329 A1 | 4/2014 | Ogiwara et al. |
| 2014/0124762 A1 | 5/2014 | Buchwald et al. |
| 2014/0138669 A1 | 5/2014 | Nakagawa et al. |
| 2014/0138870 A1 | 5/2014 | McLeod et al. |
| 2015/0155500 A1 | 6/2015 | Yersin et al. |
| 2015/0249218 A1 | 9/2015 | Yokoyama et al. |
| 2015/0270494 A1 | 9/2015 | Xu et al. |
| 2015/0280138 A1 | 10/2015 | Xu et al. |
| 2015/0340623 A1 | 11/2015 | Kawamura et al. |
| 2016/0056393 A1 | 2/2016 | Oikawa et al. |
| 2016/0064676 A1 | 3/2016 | Adachi et al. |
| 2016/0197286 A1 | 7/2016 | Kawamura et al. |
| 2016/0197287 A1 | 7/2016 | Kawamura et al. |

FOREIGN PATENT DOCUMENTS

| | | |
|---|---|---|
| CN | 103588795 A | 2/2014 |
| CN | 103694992 A | 4/2014 |
| CN | 103740359 A | 4/2014 |
| CN | 103819423 A | 5/2014 |
| EP | 2511360 A1 | 10/2012 |
| EP | 2733188 A1 | 5/2014 |
| EP | 2733761 A1 | 5/2014 |

(Continued)

OTHER PUBLICATIONS

Rubén D. Costa, et al., "Luminescent Ionic Transition-Metal Complexes for Light-Emitting Electrochemical Cells", Angew. Chem. Int. Ed. 2012, vol. 51, pp. 8178-8211.

Tao Hu, et al., "Solid-state light-emitting electrochemical cells based on ionic iridium(III) complexes" J. Mater. Chem. 2012, vol. 22, pp. 4206-4215.

Gábor Méhes, et al., "Enhanced Electroluminescence Efficiency in a Spiro-Acridine Derivative through Thermally Activated Delayed Fluorescence" Angew. Chem. Int. Ed. 2012, vol. 51, pp. 11311-11315.

Qisheng Zhang, et al., "Design of Efficient Thermally Activated Delayed Fluorescence Materials for Pure Blue Organic Light Emitting Diodes" J. Am. Chem. Soc. 2012, vol. 134, pp. 14706-14709.

(Continued)

*Primary Examiner* — Shawquia Jackson
(74) *Attorney, Agent, or Firm* — Christopher J. Knors; Moore & Van Allen PLLC

(57) ABSTRACT

Charged organic thermally activated delayed fluorescence (TADF) species are described. A light-emitting electrochemical cell (LEEC) includes the charged organic thermally activated delayed fluorescence (TADF) species and sufficient counter ions to balance the charge on the charged organic thermally activated delayed fluorescence species, as emitter material. Also disclosed are OLEDSs containing the TADF species.

17 Claims, 3 Drawing Sheets

(56) References Cited

FOREIGN PATENT DOCUMENTS

| | | |
|---|---|---|
| EP | 2733762 A1 | 5/2014 |
| WO | 2011070963 A1 | 6/2011 |
| WO | 2012133188 A1 | 10/2012 |
| WO | 2013081088 A1 | 6/2013 |
| WO | 2013092313 A1 | 6/2013 |
| WO | 2013154064 A1 | 10/2013 |
| WO | 2013172255 A1 | 11/2013 |
| WO | 2014013947 A1 | 1/2014 |
| WO | 2014024446 A1 | 2/2014 |
| WO | 2014024447 A1 | 2/2014 |
| WO | 2014024856 A1 | 2/2014 |
| WO | 2014034092 A1 | 3/2014 |
| WO | 2014038417 A1 | 3/2014 |
| WO | 2014042006 A1 | 3/2014 |
| WO | 2014076278 A2 | 5/2014 |
| WO | 2014083785 A1 | 6/2014 |
| WO | 2014092083 A1 | 6/2014 |
| WO | 2014104315 A1 | 7/2014 |
| WO | 2014104346 A1 | 7/2014 |
| WO | 2014122895 A1 | 8/2014 |
| WO | 2014163083 A1 | 10/2014 |

OTHER PUBLICATIONS

Antonio Pertegás, et al., "Light-Emitting Electrochemical Cells Using Cyanine Dyes as the Active Components" J. Am. Chem. Soc. 2013, vol. 135, pp. 18008-18011.

Sae Youn Lee, et al., "Luminous Butterflies: Efficient Exciton Harvesting by Benzophenone Derivatives for Full-Color Delayed Fluorescence OLEDs" Angew. Chem. Int. Ed. 2014, vol. 53, pp. 6402-6406.

Ye Tao, et al., "Thermally Activated Delayed Fluorescence Materials Towards the Breakthrough of Organoelectronics", Advanced Materials, 2014, vol. 26, pp. 7931-7958.

Thomas J. Penfold "On Predicting the Excited-State Properties of Thermally Activated Delayed Fluorescence Emitters" J. Phys. Chem. 2015, vol. 119, pp. 13535-13544.

Michael Y. Wong, et al., "Light-Emitting Electrochemical Cells and Solution-Processed Organic Light-Emitting Diodes Using Small Molecule Organic Thermally Activated Delayed Fluorescence Emitters" Chem. Mater. 2015, vol. 27 (19), pp. 6535-6542.

Hiroki Uoyama, et al., "Highly efficient organic light-emitting diodes from delayed fluorescence" Nature 2012, vol. 492, pp. 234-240.

Hajime Nakanotani, et al., "High-efficiency organic light-emitting diodes with fluorescent emitters" Nat. Commun. 2014, vol. 5, pp. 4016-4022.

Sebastian Reineke, "Organic Light Emitting Diodes: Phosphorescence meets its match" Nature Photonics 2014, vol. 8, pp. 269-270.

Qisheng Zhang, et al., "Efficient blue organic light emitting diodes employing thermally activated delay fluorescence", Nature Photon. 2014, vol. 8, pp. 326-332.

IPO; Great Britain Search Report for British Application No. GB1423289.6 dated Nov. 2, 2015, 3 pages.

WIPO; International Search Report and Written Opinion for International Application No. PCT/GB2015/054172 dated Jan. 2015, 9 pages.

Chinese Patent Office; Office Action for Chinese Patent Application No. 201580077055.5 dated Sep. 7, 2018, 8 Pages.

LIGHT EMITTING ELECTROCHEMICAL CELLS AND COMPOUNDS

CROSS-REFERENCE TO RELATED APPLICATIONS

This application is a 35 U.S.C. § 371 National Stage Application of International Application No. PCT/GB2015/054172, filed Dec. 29, 2015, which claims the benefit of British Application No. 1507337.2 filed on Apr. 29, 2015, which claims the benefit of British Application No. 1423289.6 filed on Dec. 29, 2014, the entirety of each of which is incorporated herein by reference.

FIELD OF THE INVENTION

The present invention is directed to the provision of Light Emitting Electrochemical Cells (LEECs) and luminescent emitter compounds for use in LEECs, in particular to Thermally Activated Delayed Fluorescence (TADF) compounds for use in LEECs or other light emitting devices.

BACKGROUND TO THE INVENTION

Organic Light Emitting Diodes (OLEDs) have come to the fore as the state-of-the-art technology for visual displays and lighting. OLEDs are desirable as they are light weight, flexible, provide better contrast and possess large viewing angle. OLEDs are also more power efficient than traditional lighting sources and thus their wide adoption can alleviate significantly the strain on current energy demand because lighting alone constitutes about 20% of energy consumption worldwide.

The "first generation" OLEDs were based on organic fluorescent emitters whose efficiency was intrinsically capped at 25% due to only being able to recruit singlet excitons. The "second generation" OLEDs employed organometallic phosphorescent emitters, which harvest both singlet and triplet excitons for emission due to the enhanced intersystem crossing (ISC) mediated by the large spin-orbit coupling of heavy metals such as iridium(III) and platinum (II). Despite their highly desirable performance characteristics, the rarity of these metals, their high cost and their toxicity are important detracting features that inhibit large-scale, worldwide adoption of OLED technology.

The "third generation" OLEDs were recently first reported by Adachi and co-workers. His group demonstrated how small organic molecules, emitting via a thermally activated delayed fluorescence (TADF) mechanism, could be integrated into OLEDs and exhibit very high efficiencies as, like with phosphorescent emitters, both singlet and triplet excitons are recruited for emission (Reference 1). Thus, TADF-based OLEDs address the key detracting features endemic to "second generation" OLEDs while retaining their advantages (Reference 2).

The principle of TADF relies on a small energy gap between the lowest singlet and triplet excited states ($\Delta E_{ST}$). Under these conditions, the electrons in the triplet state can return to the singlet state by reverse intersystem crossing (RISC) using thermal energy, followed by radiative fluorescence (Reference 1a). The small $\Delta E_{ST}$ is realized by spatial separation between HOMO and LUMO to minimize the electronic repulsion between these orbitals. A large number of organic TADF emitters have been reported to date. They can make use of donor and acceptor moieties of various types within the molecule to achieve the desired small energy gap between the lowest singlet and triplet excited states ($\Delta E_{ST}$). The majority of these molecules are based on a twisted intramolecular charge transfer (TICT) design in which the donor and acceptor moieties are designed to be nearly orthogonal to each other (References 1a, 1c and 3).

However, current OLEDs, including TADF-OLEDs, still employ air sensitive electrodes requiring encapsulation, are vacuum deposited limiting the size of the device, and possess a complex multi-layer architecture that add to the cost of fabrication.

Single-layer solid-state light-emitting electrochemical cells (LEECs) have received much recent attention for their potential to address these negative design features found in OLEDs (Reference 4). The emitters in LEECs are frequently ionic transition metal complexes, the most popular and highest performing class of which are cationic iridium(III) complexes.

As with their use in OLEDs the use of rare heavy metal complexes in LEECs presents challenges. As an alternative to small molecule emitters for LEECs can include conjugated polymers together with ion transport material and inorganic salts such as LiOTf. Recently a first example of an operational LEEC with a small-molecule organic cyanine dye based fluorophore as an alternative to iridium based complexes has been disclosed (Reference 5).

Despite the progress made there is a need to provide improved and alternative compounds for use in display and lighting uses, such as in light emitting electrochemical cells (LEECs).

DESCRIPTION OF THE INVENTION

According to a first aspect the present invention provides a light-emitting electrochemical cell (LEEC) comprising: a charged organic thermally activated delayed fluorescence (TADF) species and sufficient counter ions to balance the charge on the charged organic thermally activated delayed fluorescence (TADF) species; or mixtures thereof, as emitter material.

The electroluminescent material of the LEEC may comprise, consists of, or consist essentially of the charged organic thermally activated delayed fluorescence (TADF) species and sufficient counter ions to balance the charge on the TADF species.

These organic salts (organic charged TADF species and counter ions) can be used in LEECs but also in other electroluminescent devices such as OLEDs. They may also be employed in applications using their photoluminescence properties. The salts and their other uses also constitute further aspects of the invention.

Mixtures of charged TADF species and/or counter ions may be employed. Other emitter materials may additionally be employed.

More than one TADF chromophore may be employed in the charged TADF species, for example one two or three TADF chromophores of the known types may be bonded together in a molecule and provided with charge and corresponding counter ions.

According to a second aspect the present invention also provides a method of producing light, the method comprising:
providing a charged organic thermally activated delayed fluorescence (TADF) species and sufficient counter ions to balance the charge on the charged organic thermally activated delayed fluorescence (TADF) species; or mixtures thereof;
manufacturing an electroluminescent device including the charged organic TADF species and sufficient counter ions to balance the charge on the charged organic TADF species; or mixtures thereof as emitter material; and operating the electroluminescent device.

The electroluminescent device may be an OLED or a LEEC for example.

TADF species may be derived from the discrete uncharged TADF molecules that are well known in the art, for example those described in patent documents describing options for TADF chromophores: CN103694992, CN103819423, EP02733761, US2014/0124762, US2013/0306945, US2014/0103329, US2014/0138669, WO2012133188, WO2013180261, WO2014013947, WO2014024446, WO201424447, WO2014034092, WO2014038417, WO2014042006, WO2014083785, WO2014092083, WO2014104346, WO2014122895, WO2013092313, EP2511360, EP2733762, U.S. Pat. No. 8,847,218, US20120241732, US2014138870, WO2011070963, WO2013081088, WO2013154064, WO2013172255, WO2014024856, and WO2014104315. The contents of these documents are incorporated by reference herein. Alternatively the charged TADF species may be a polymer for example.

The charged organic thermally activated delayed fluorescence (TADF) species does not contain a metal, although the counter ions may be metal cations if the TADF species is negatively charged. For example alkali metal cations. This absence of metal in the organic TADF species provides benefits in terms of cost and can avoid toxicity caused by the presence of heavy metals. The TADF species can provide the benefits in terms of high efficiencies found with OLED devices but in use in a LEEC, by virtue of the charge and corresponding counter ions. The charged organic thermally activated delayed fluorescence (TADF) species and its accompanying counter ions can present the advantage of good solubility allowing solution processing, for example inkjet type printing when fabricating display devices, especially when fabricating large displays. The benefits of solution processing can be employed when fabricating OLEDs or LEECs. Other benefits of LEECs can be realised, such as the ability to fabricate the device in air and the ability to use air stable electrodes.

The emitter material of the light-emitting electrochemical cell (LEEC) may comprise, consist of, or consist essentially of a TADF species that includes a charged substituent or charged substituents. The charged substituents may be an integral part of the TADF species i.e. the charged substituent may exhibit or contribute to either acceptor or donor behaviour that provides the TADF effect.

For example where cyanobenzene moieties are used as acceptor moieties to complement carbazole moieties as donor moieties for TADF (e.g. reference 1a), alternatives to cyano substituents to achieve acceptor behaviour can include carboxylate (—CO$_2^-$), sulfonate (—SO$_3^-$) phosphate (—PO$_4^-$), quaternary ammonium (—NR$_3^+$) or phosphonium (—PR$_3^+$) as discussed in more detail and with reference to a particular embodiment hereafter. The substituents R on the nitrogen or phosphorus may be independently for each occurrence selected from H, alkyl, aryl or heteroaryl (for example substituted or unsubstituted C1-C20 or even C1-C10).

An electron withdrawing group of the acceptor portion of the molecule is charged, allowing the option of using the emitter material in a LEEC.

Similarly, charged substituents (such as may contribute donor behaviour to the overall TADF effect.) may be provided as part of a donor portion of a TADF molecule. For example, alkoxide (—RO$^-$ or thiolate (—RS$^-$). The groups R connecting to the rest of the TADF species may be selected from hydrocarbylene chains, for example C1 to C30 or even C1 to C10, that may be substituted or unsubstituted hydrocarbylene or unsaturated hydrocarbylene. The hydrocarbylene chain can include substituted or unsubstituted saturated, unsaturated or aromatic rings.

Alternatively the charged species may be distinct from the TADF effect but supplied as charged substituents bonding to the TADF species without contributing to or contributing substantially to the TADF effect of the chromophore.

Thus for example the emitter material of the light-emitting electrochemical cell (LEEC) may comprise, consist of, or consist essentially of a compound according to formula I:

$$\text{TADF}(-Y^p)_n mA^q \qquad \text{I}$$

wherein TADF is an organic thermally activated delayed fluorescence moiety;

Y is a metal free charged species bonded to the TADF moiety;

n is at least 1;

A is a counter ion;

p and q are the charges on each Y and A respectively; and m is the number of counter ions A, wherein p×n=m×q.

The counter ion A is oppositely charged with respect to the metal free charged species Y to balance charge. The charged species Y may be bonded directly to the TADF moiety. Conveniently the charged species Y includes a charged group and a linking group that bonds the charged group to the TADF moiety. Use of a linking group provides a modular route to functionalization of TADF chromophores for applications in LEECs. Thus the use of a linking group or groups with an attached charged group allows the potential to use any of the wide range of TADF moieties that are already known, for example in the documents discussed above.

Thus a compound of formula I may take the form of formula II:

$$\text{TADF}(-L-Z^p)_n mA^q \qquad \text{II}$$

wherein the metal free charged species Y is a non-metal charged group Z and optional linking group L; and wherein TADF, A, n, m, p and q have the same meaning as in formula I.

The linking group L is optional for each occurrence of groups Z. Conveniently where linking groups L are employed, one is used for each group Z.

Where present the linking group L may, independently for each occurrence, comprise or consist of a hydrocarbylene chain, for example C1 to C30 or even C1 to C10, that may be substituted or unsubstituted, hydrocarbylene or unsaturated hydrocarbylene. The hydrocarbylene chain can include substituted or unsubstituted saturated, unsaturated or aromatic rings. For example the hydrocarbylene chain may include or consist of substituted or unsubstituted cyclopentane-1,3-diyl, cyclohexane-1,4-diyl, 1,4-phenylene or 4,4'-biphenylene moieties. Aromatic rings where present may be aryl or heteroaryl.

Where the linking group L is substituted it may be independently substituted for each occurrence. For example once, twice, or three times, e.g. once, i.e. formally replacing one or more hydrogen atoms of the hydrocarbylene chain. Examples of such substituents are halo (e.g. fluoro, chloro, bromo and iodo), —SF$_5$, —CF$_3$, —OMe, —NO$_2$, substituted or unsubstituted primary, secondary or tertiary alkyl, that may be cyclic and may be unsaturated (for example C1-C10 or even C1-C4); substituted or unsubstituted aryl or heteroaryl, aryl hydroxy, amino, alkoxy, alkylthio, carboxy, cyano, thio, formyl, ester, acyl, thioacyl, amido, sulfonamido, carbamate, phosphine oxide, phosphine sulphide and the like. Where the substituent is amino it may be $NH_2$, NHR or $NR_2$, where the substituents R on the nitrogen may be alkyl, aryl or heteroaryl (for example substituted or unsubstituted C1-C20 or even C1-C10).

In addition to substitution options for linking groups L as discussed above, similar options for substitution may be employed for other groups or substituents that may be substituted or unsubstituted as described herein. Thus groups that may be substituted may be, for example, substituted once, twice, or three times, e.g. once, i.e. formally replacing one or more hydrogen atoms of the group. Examples of such substituents are halo (e.g. fluoro, chloro, bromo and iodo), —$SF_5$, —$CF_3$, —OMe, —$NO_2$, substituted or unsubstituted primary, secondary or tertiary alkyl, that may be cyclic and may be unsaturated (for example C1-C10 or even C1-C4); substituted or unsubstituted aryl or heteroaryl, aryl hydroxy, amino, alkoxy, alkylthio, carboxy, cyano, thio, formyl, ester, acyl, thioacyl, amido, sulfonamido, carbamate, phosphine oxide, phosphine sulphide and the like. Where the substituent is amino it may be $NH_2$, NHR or $NR_2$, where the substituents R on the nitrogen may be alkyl, aryl or heteroaryl (for example substituted or unsubstituted C1-C20 or even C1-C10).

By aryl is meant herein a radical formed formally by abstraction of a hydrogen atom from an aromatic compound. As known to those skilled in the art, heteroaryl moieties are a subset of aryl moieties that comprise one or more heteroatoms, typically O, N or S, in place of one or more carbon atoms and any hydrogen atoms attached thereto. Exemplary aryl substituents, for example, include phenyl or naphthyl that may be substituted. Exemplary heteroaryl substituents, for example, include pyridinyl, furanyl, pyrrolyl and pyrimidinyl.

Further examples of heteroaromatic rings include pyridazinyl (in which 2 nitrogen atoms are adjacent in an aromatic 6-membered ring); pyrazinyl (in which 2 nitrogens are 1,4-disposed in a 6-membered aromatic ring); pyrimidinyl (in which 2 nitrogen atoms are 1,3-disposed in a 6-membered aromatic ring); or 1,3,5-triazinyl (in which 3 nitrogen atoms are 1,3,5-disposed in a 6-membered aromatic ring).

Where the linking group includes one or more rings they may be cycloalkyl they may be for example cyclohexyl or cyclopentyl rings. The cyclohexyl or cyclopentyl groups if present may be saturated or unsaturated and may be substituted as described above.

A linking group L may also include heteroatoms in a hydrocarbylene chain, for example by substituting one or more carbon atoms in the chain e.g. one, two, or three carbon atoms with any one of O, N, or S for example.

Examples of unsubstituted hydrocarbylene chains for group L include:

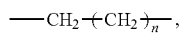

wherein n is from 0 to 10 or even 0 to 5 and optionally containing one or more unsaturations; cyclopentane-1,3-diyl; cyclohexane-1,4-diyl; 1,4-phenylene; 4,4'-biphenylene.

Non-metal charged groups Z may be, independently for each occurrence, positively or negatively charged. Counter ions A will have the opposite charge. For example where charged groups Z are singly charged and counter ions A are also singly charged then compounds of formula II may take either the form of formula III or of formula IV:

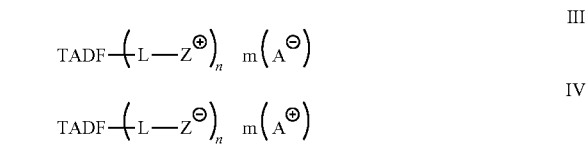

where n=m.

Where groups Z are positively charged they may be, independently for each occurrence, selected from the group consisting of quaternary nitrogen cations, and quaternary phosphorus cations. Conveniently all groups Z will be the same.

Where groups Z are negatively charged they may be provided with anionic substituents such as carboxylate, sulfonate, sulfinate, phosphonate, cyanide and thiocyanate.

Examples of quaternary nitrogen groups Z include:

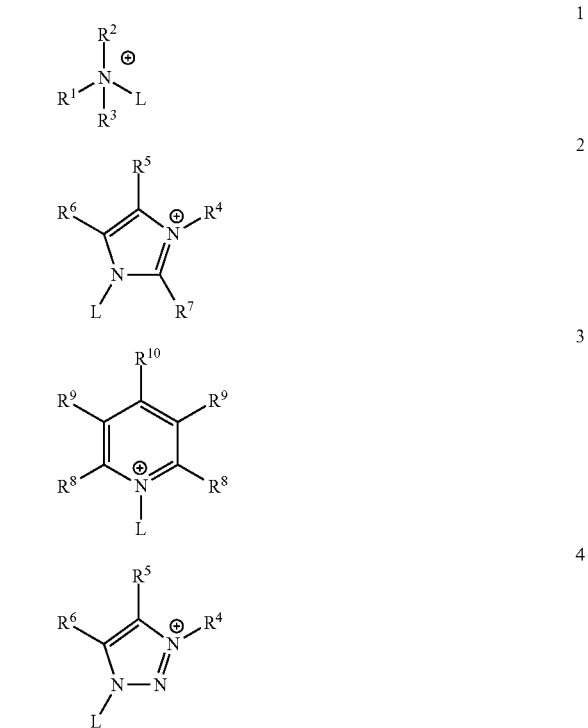

wherein -L indicates the position of bonding to a linking group L or directly to a TADF moiety; $R^1$, $R^2$, $R^3$, $R^4$, $R^5$, $R^6$, $R^7$, $R^8$, $R^9$ and $R^{10}$ are, independently for each occurrence, selected from the group consisting of —H, substituted or unsubstituted primary, secondary or tertiary alkyl, that may be cyclic and may be unsaturated (for example C1-C10 or even C1-C4); substituted or unsubstituted aryl or heteroaryl, —$CF_3$, —OMe, —$SF_5$, —$NO_2$, halo (e.g. fluoro, chloro, bromo and iodo), aryl, aryl hydroxy, amino, alkoxy, alkylthio, carboxy, cyano, thio, formyl, ester, acyl, thioacyl, amido, sulfonamido, carbamate and the like. Where the substituent is amino it may be $NH_2$, NHR or $NR_2$, where the substituents R on the nitrogen may be alkyl, aryl or heteroaryl (for example substituted or unsubstituted C1-C20 or even C1-C10).

Where the quaternary nitrogen is pyridynyl as in structure 3 the attachment to linking group L or directly to a TADF moiety may be to a carbon rather than to the nitrogen, Thus the quaternary nitrogen group Z may take the form of structure 5:

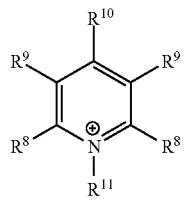

5 wherein one of $R^8$, $R^9$, $R^{10}$ and $R^{11}$ bonds to a linking group L or directly to a TADF moiety and the others of $R^8$, $R^9$, $R^{10}$ and $R^{11}$, independently for each occurrence selected from the group consisting of —H, substituted or unsubstituted primary, secondary or tertiary alkyl, that may be cyclic and may be unsaturated (for example C1-C10 or even C1-C4); substituted or unsubstituted aryl or heteroaryl, —$CF_3$, —OMe, —$SF_5$, —$NO_2$, halo (e.g. fluoro, chloro, bromo and iodo), aryl, aryl hydroxy, amino, alkoxy, alkylthio, carboxy, cyano, thio, formyl, ester, acyl, thioacyl, amido, sulfonamido, carbamate and the like. Where the substituent is amino it may be $NH_2$, NHR or $NR_2$, where the substituents R on the nitrogen may be alkyl, aryl or heteroaryl (for example substituted or unsubstituted C1-C20 or even C1-C10).

Where groups $R^1$, $R^2$, $R^3$, $R^4$, $R^5$, $R^6$, $R^7$, $R^8$, $R^9$ and $R^{10}$ are aryl, heteroaryl or cycloalkyl and are substituted, they may be substituted with substituted or unsubstituted primary, secondary or tertiary alkyl, that may be cyclic and may be unsaturated (for example C1-C10 or even C1-C4); substituted or unsubstituted aryl or heteroaryl, —$CF_3$, —OMe, —$SF_5$, —$NO_2$, halo (e.g. fluoro, chloro, bromo and iodo), aryl, aryl hydroxy, amino, alkoxy, alkylthio, carboxy, cyano, thio, formyl, ester, acyl, thioacyl, amido, sulfonamido, carbamate and the like. Where the substituent is amino it may be $NH_2$, NHR or $NR_2$, where the substituents R on the nitrogen may be alkyl, aryl or heteroaryl (for example substituted or unsubstituted C1-C20 or even C1-C10).

Thus examples of quaternary nitrogen groups Z include:

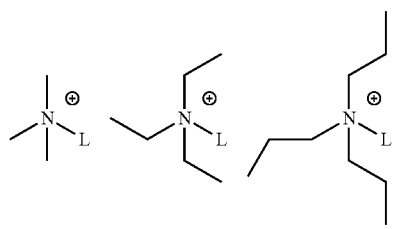

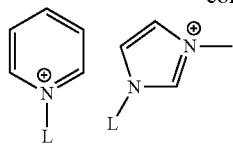

wherein -L indicates the position of bonding to a linking group L or directly to a TADF moiety.

Examples of quaternary phosphorus groups Z include:

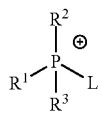

6 wherein $R^1$, $R^2$ and $R^3$ have the same meaning as for the corresponding quaternary nitrogen group 1 discussed above and wherein -L indicates the position of bonding to a linking group L or directly to a TADF moiety.

Thus examples of quaternary phosphorus groups Z include:

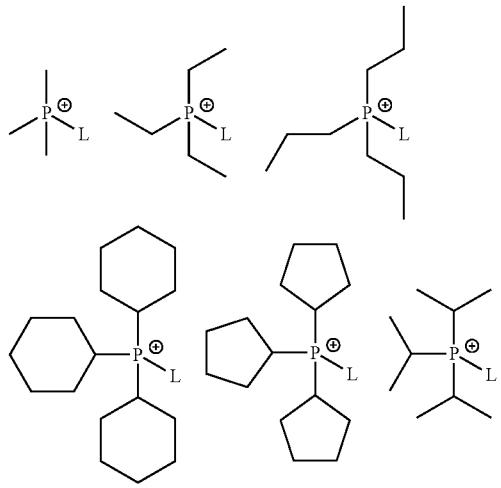

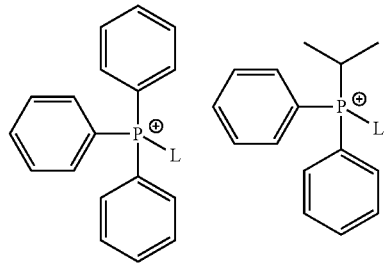

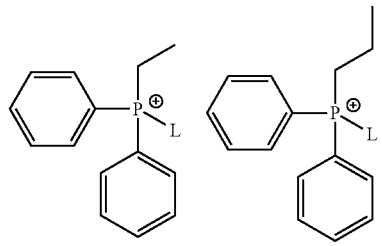

wherein -L indicates the position of bonding to a linking group L or directly to a TADF moiety.

Many suitable TADF molecules are known for proposed use as emitter material in OLED devices. Reference 6 describes TADF materials and includes discussion of wide range of metal free TADF molecules. Such TADF molecules can find use as TADF core structures (chromophores) in the TADF species of compounds employed in the LEECs of the present invention.

Typically the TADF species will have a small difference in energy gap between singlet and triplet ($S_1$ and $T_1$) exited states that is <100 meV ($\Delta E_{ST}$<100 mEv).

Examples of suitable TADF core structures are described in the references where carbazoyl dicyanobenzene (CDCB) TADF emitter molecules are described. In these molecules carbazole (or derivative) acts as electron donor and dicyanobenzene (or derivative) as electron acceptor. The HOMO on the donor and the LUMO on the acceptor are localised, having minimal overlap due to distortion of carbazole out of the plane of the dicyanobenzene caused by steric hindrance. This provides a desirable small $\Delta E_{ST}$. More generally TADF structures have an electron donor linked to an electron acceptor, typically via a conjugative linker.

The TADF moiety in a compound used as emitter material of the invention may include more than one TADF chromophore, for example one to three TADF chromophores, such as carbazoyl dicyanobenzene (CDCB) chromophores, bonded together.

However only one TADF chromophore may be employed to provide the TADF effect.

For example a charged derivative of a TADF species according to formula V:

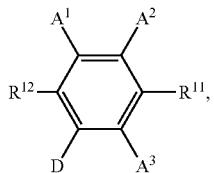

V wherein D is a donor moiety of the form;

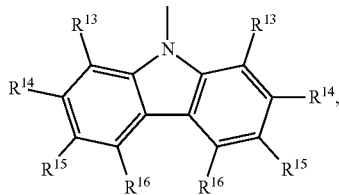

wherein each of $A^1$, $A^2$, and $A^3$ are acceptor groups that may be same or different and are independently selected from the group consisting of —CN, —$CO_2^-$, —$CO_2R^*$, —$SO_3^-$, —$PO_4^-$, —$NR_3^+$, —$PR_3^+$, halogen (F, Cl, Br, I), wherein R* and the substituents R on $^-$, —$NR_3^+$ and —$PR_3^+$, may be independently for each occurrence selected from H, alkyl, aryl or heteroaryl (for example substituted or unsubstituted C1-C20 or even C1-C10); and —$CO_2$-L-Z wherein L is an optional linking group and Z a charged group, each L if present and each Z having, independently for each occurrence, the same meanings as discussed above for compounds of formulas II, III or IV;

wherein, when none of $A^1$, $A^2$, and $A^3$ are charged, at least one of the occurrences of $R^{11}$, $R^{12}$, $R^{13}$, $R^{14}$, $R^{15}$ and $R^{16}$ represents the bonding position, either directly or via a linking group L, to a charged group Z, each L if present and each Z having, independently for each occurrence, the same meanings as discussed above for compounds of formulas II, III or IV; and wherein each group $R^{11}$, $R^{12}$, $R^{13}$, $R^{14}$, $R^{15}$ and $R^{16}$ not involved in bonding to an organic charged group Z is, independently for each occurrence, selected from the group consisting of —H, substituted or unsubstituted primary, secondary or tertiary alkyl, that may be cyclic and may be unsaturated (for example C1-C10 or even C1-C4); substituted or unsubstituted aryl or heteroaryl, —$CF_3$, —OMe, —$SF_5$, —$NO_2$, halo (e.g. fluoro, chloro, bromo and iodo), aryl, aryl hydroxy, amino, alkoxy, alkylthio, carboxy, cyano, thio, formyl, ester, acyl, thioacyl, amido, sulfonamido, carbamate, phosphine oxide, phosphine sulphide and the like.

Where the group is amino it may be —$NH_2$, —NHR or —$NR_2$, where the substituents R on the nitrogen may be alkyl, aryl or heteroaryl (for example substituted or unsubstituted C1-C20 or even C1-C10).

Where the group is phosphine oxide or phosphine sulphide it may be selected from the group consisting of:

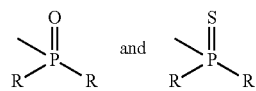

where the substituents R on the phosphorus may be substituted or unsubstituted alkyl, aryl or heteroaryl (for example substituted or unsubstituted C1-C20 or even C1-C10).

The phosphine oxide or phosphine sulphide substituent may be para to the nitrogen of the carbazole structure i.e. one or both of $R^{15}$ may be a phosphine oxide or phosphine sulphide substituent. Conveniently where both $R^{15}$ are a phosphine oxide or phosphine sulphide substituent they may be the same. The phosphine oxide or phosphine sulphide substituent may have phenyl or substituted phenyl groups R on the phosphorus.

Thus substituents:

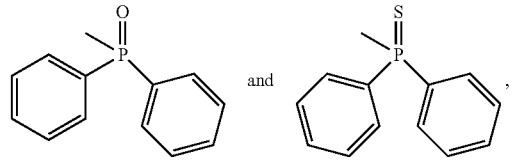

or substituents where one or both phenyl groups are substituted, are contemplated for donor moieties D.

Phosphine oxide or phosphine sulphide may be used as acceptor moieties, or part of acceptor moieties (substituents on acceptor moieties) in the structure of a TADF molecule, such as the TADF compounds described herein.

Where used as a substituent on a donor moiety D as described herein, phosphine oxide or phosphine sulphide acts to moderate the character of the donor and can therefore alter the photo physical behaviour of a TADF compound, for example resulting in a change in colour and or intensity of emission.

Phosphine oxide and phosphine sulphide substituents may be introduced, for example, in accordance with the Scheme below which illustrates substitution on carbazole, a typical donor moiety:

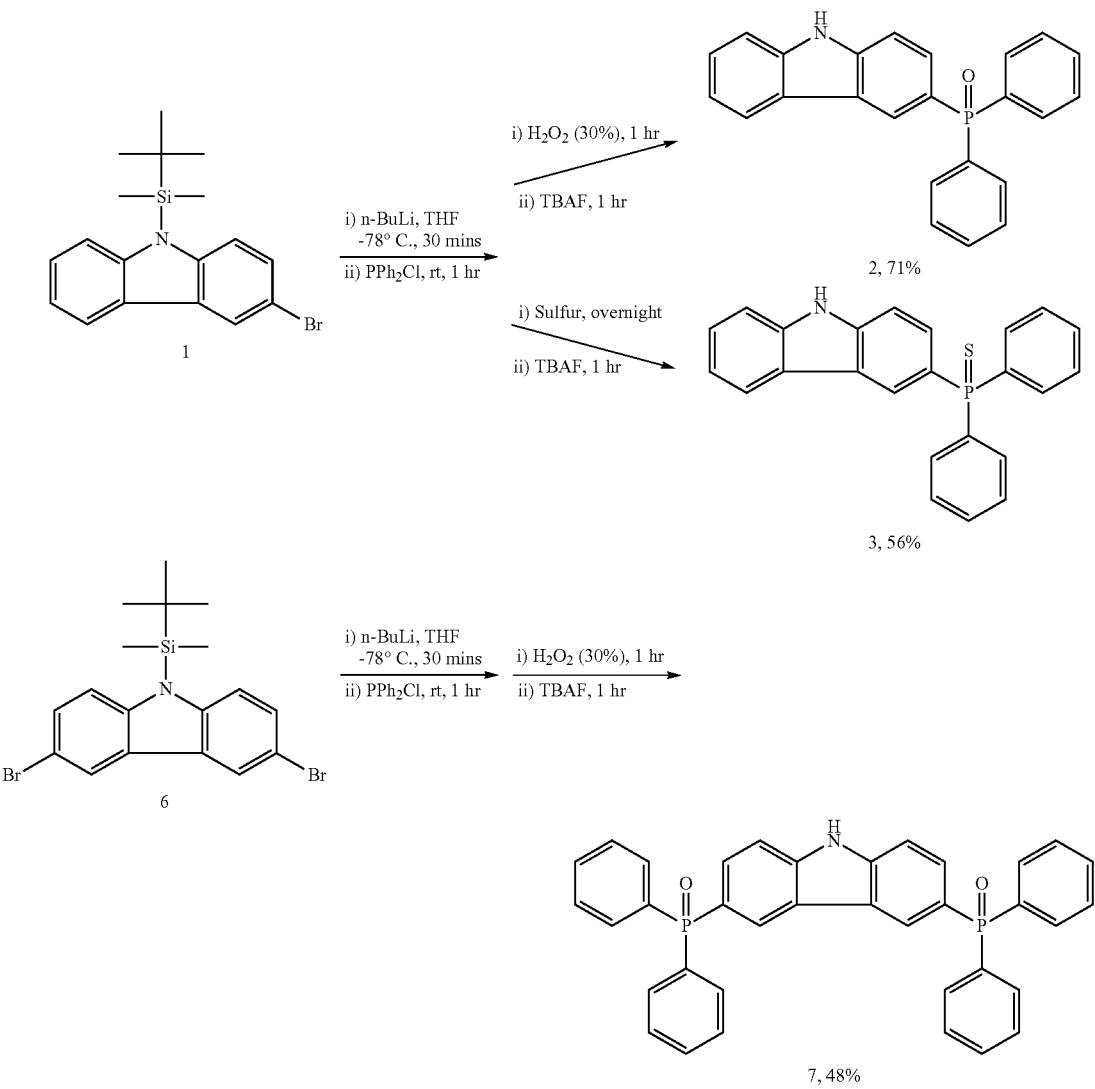
Advantageously groups $A^1$ and $A^2$ may be the same and $A^3$ different, as the synthetic route is generally less complex. For example, $A^1$ and $A^2$ may both be —CN and $A^3$ may be —F.
More generally moieties D may also be selected from:
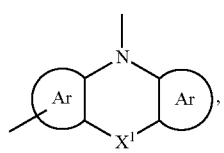
A
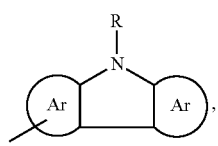
B
-continued
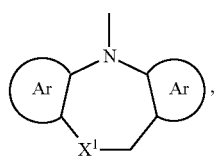
C
D
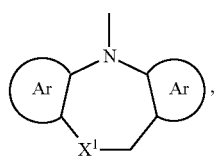
E -continued

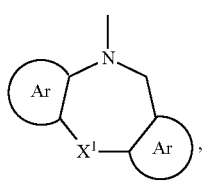, F .

At least one charged group Z is provided on —Ar or

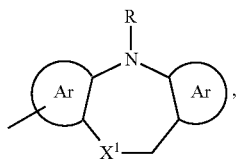, G .

when not provided elsewhere on the charged organic thermally activated delayed fluorescence (TADF) species.

Substituents on —Ar and

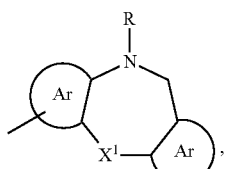, H , where present can include phosphine oxide or phosphine sulphide, to moderate the donor properties.

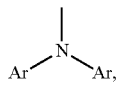

Thus donor moieties D in a compound of formula V may also be selected from:

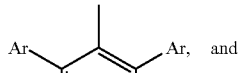 and

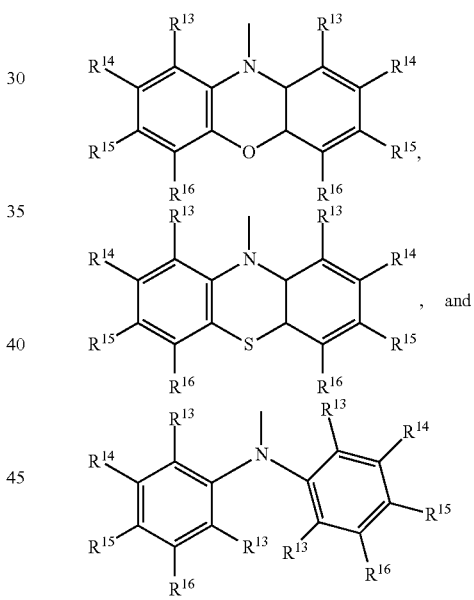

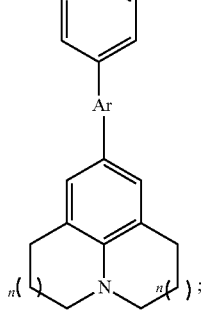;

wherein X¹ is selected from the group consisting of O, S, NR, SiR$_2$, PR and CR$_2$, wherein each R is independently selected from the group consisting of —H, alkyl, aryl or heteroaryl (for example substituted or unsubstituted C1-C20 or even C1-C10);

each Ar is independently for each occurrence selected from the group consisting of substituted or unsubstituted aryl or heteroaryl; and

represents, independently for each occurrence a substituted or unsubstituted aryl or heteroaryl ring fused to the central ring of structures A B, C, D, E or F, for example a five or a six membered substituted or unsubstituted aryl or heteroaryl ring, and in structures C, D, G and H bonding to the rest of the molecule is para to the nitrogen;

n ( ) indicates the optional presence of saturated —CH$_2$— groups in the rings annelated to the benzene ring, wherein n is independently for each occurrence, 0, 1, or 2; and optionally at least one charged group Z, optionally via a linking group L, is provided as a substituent on —Ar or wherein the groups $R^{13}$, $R^{14}$, $R^{15}$ and $R^{16}$ may take the same meaning as before; groups.

The saturated rings annelated to the benzene ring in the structure:

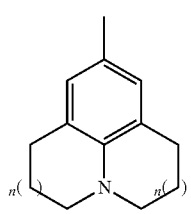

may be five six or seven membered rings. Typically they may be six membered, i.e. the juliolidine structure:

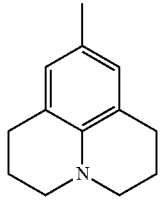

For further example charged derivatives of dicyanobenzene with carbazoyl TADF moieties according to formula Va or formula VI:

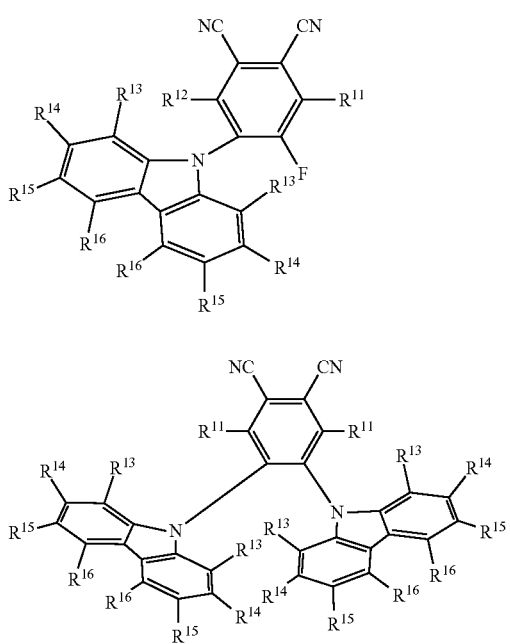

wherein at least one of the occurrences of $R^{11}$, $R^{12}$, $R^{13}$, $R^{14}$, $R^{15}$ and $R^{16}$ represents the bonding position, either directly or via a linking group L, to a charged group Z, each L if present and each Z having, independently for each occurrence, the same meanings as discussed above for compounds of formula III or IV; and wherein each group $R^{11}$, $R^{12}$, $R^{13}$, $R^{14}$, $R^{15}$ and $R^{16}$ not involved in bonding to an organic charged group Z is, independently for each occurrence, selected from the group consisting of —H, substituted or unsubstituted primary, secondary or tertiary alkyl, that may be cyclic and may be unsaturated (for example C1-C10 or even C1-C4); substituted or unsubstituted aryl or heteroaryl, —CF$_3$, —OMe, —SF$_5$, —NO$_2$, halo (e.g. fluoro, chloro, bromo and iodo), aryl, aryl hydroxy, amino, alkoxy, alkylthio, carboxy, cyano, thio, formyl, ester, acyl, thioacyl, amido, sulfonamido, carbamate, phosphine oxide, phosphine sulphide and the like. Where the substituent is amino it may be NH$_2$, NHR or NR$_2$, where the substituents R on the nitrogen may be alkyl, aryl or heteroaryl (for example substituted or unsubstituted C1-C20 or even C1-C10).

Conveniently the TADF moieties according to formula Va or formula VI bond to a charged group Z via at least one of the positions $R^{15}$ (para to the carbazole nitrogen).

Conveniently both carbazole structures in the TADF moieties of formula VI have the same substitution pattern.

Thus LEECs may include compounds using TADF species of formula III or formula IV that may for example take the form of formulas VII, VIII or VIIIa:

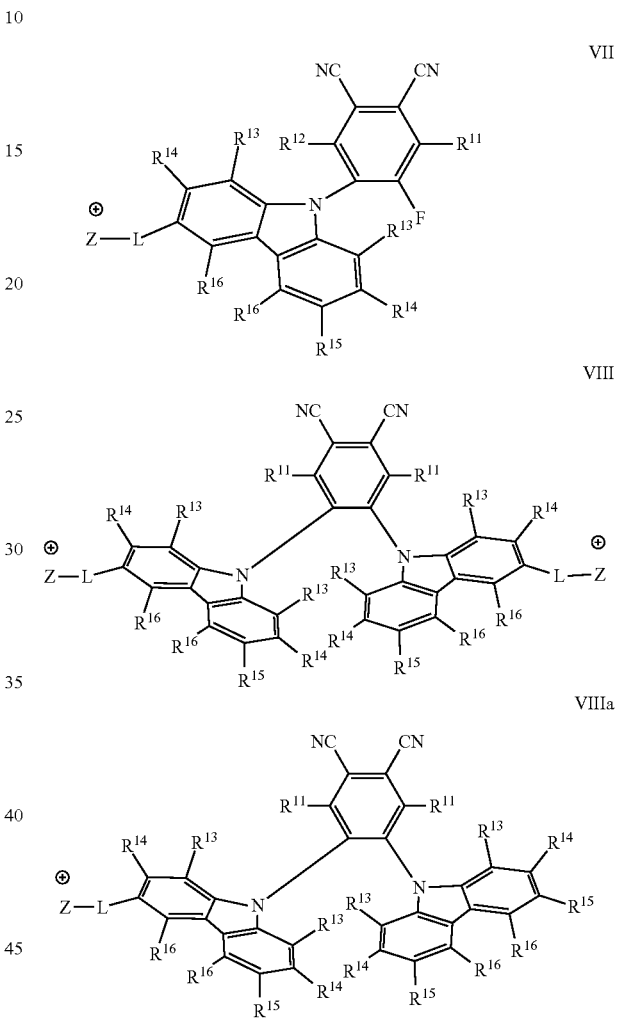

wherein the groups $R^{11}$, $R^{12}$, $R^{13}$, $R^{14}$, $R^{15}$ and $R^{16}$ take the same meaning as discussed above, whennot involved in bonding to an organic group Z; linking group L may be present or absent and if present may take the form discussed above with respect to formula II; Z is a monocationic metal free charged group such as described herein. Counter ions A as described herein are provided to counter charges Z, for example mono anionic species A⁻ such as described herein.

More generally structures such as formulas VII and VIII are also contemplated where groups Z include more than one charge and/or are anionic. Counter ions A are provided to carry counter charges to those on groups Z and be provided to achieve charge balance as for general formula I. Thus counter ions A may carry more than one charge e.g. 2⁺ or 3⁺.

When anionic counter ions A in compounds of the invention may be, independently for each occurrence selected from the group consisting of halide (chloride fluoride, bromide or iodide), PF$_6$⁻, BF$_4$⁻, BR$_4$⁻, OTf⁻, OTs⁻, SbX$_6$⁻, $NTf_2^-$, $NO_3^-$, and $CO_3^{2-}$. X is halide (fluoride, chloride, bromide or iodide) and R is an aryl group, for example phenyl. Where A is halide it may conveniently be F. Anionic counter ions A employed may be mixed, for example a mixture of fluoride and chloride maybe employed.

When cationic counter ions A in compounds of the invention may be, independently for each occurrence selected from the group consisting of cations of first and second group elements in the periodic table and quaternary ammonium cations. Cationic counter ions A employed may be mixed, for example a mixture of lithium and sodium ions maybe employed.

Thus for example cationic counter ions A may be selected from $Li^+$, $K^+$, $Na^+$ $Mg^{2+}$, $Ca^{2+}$ and $NR_4^+$. When $NR_4^+$ the groups R of the quaternary ammonium salt may be, independently for each occurrence selected from the group consisting of —H, alkyl (primary secondary or tertiary), aryl and heteroaryl. Alkyl, aryl or heteroaryl substituents may be saturated or unsaturated, and substituted or unsubstituted. Primary, secondary or tertiary alkyl, may be cyclic and may be unsaturated (for example C1-C10 or even C1-C4).

According to a further aspect the present invention provides a charged organic thermally activated delayed fluorescence (TADF) species and sufficient counter ions to balance the charge on the charged organic thermally activated delayed fluorescence (TADF) species as described herein. These organic salts can find use as emitter material in a light-emitting electrochemical cell (LEEC). These organic salts may be in accordance with formula I and the various other options described herein. These organic salts may be employed as or as part of the light emitting material in other devices, such as OLEDs for example. The charged organic thermally activated delayed fluorescence (TADF) species is metal free but may have metal counter ions as described herein.

Examples of compounds of formulas VII and VIII include compounds of formulas IX and X:

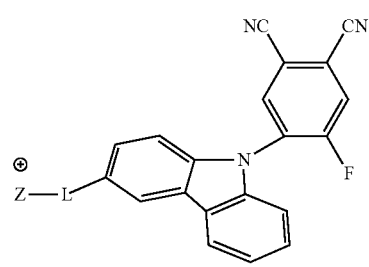

IX

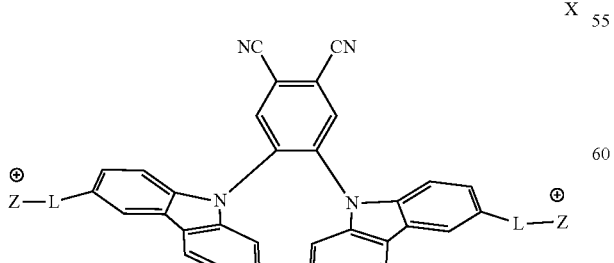

X wherein for each occurrence L is absent or is independently selected from the group consisting of:

$$-CH_2-(CH_2)_n-,$$

wherein n is from 0 to 10 or even from 0 to 7;

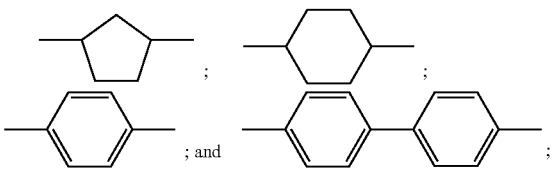

; and wherein for each occurrence Z is independently selected from the group consisting of:

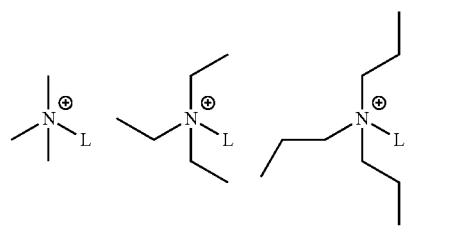

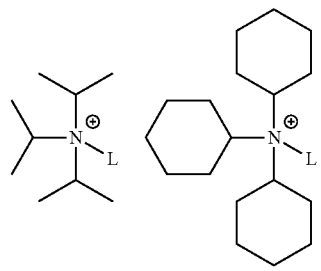

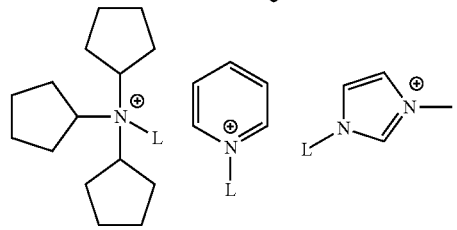

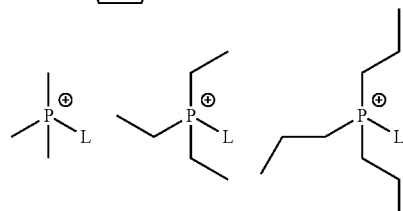

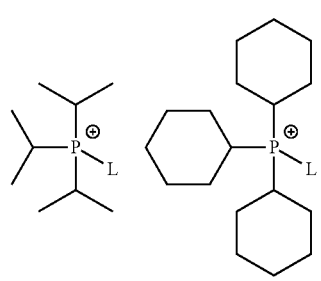

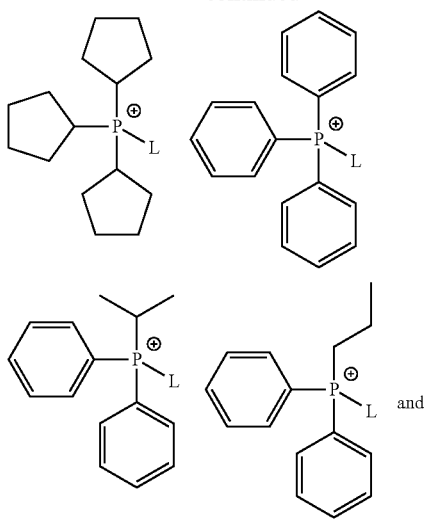 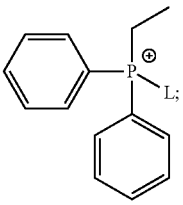

wherein -L indicates the indicates the position of bonding to linking group L or directly to the carbazole ring if L is absent.

Counter ions A may be independently for each occurrence selected from the group consisting of $PF_6^-$, $BF_4^-$ and $F^-$. Other counter ions a may be used as described herein.

Conveniently in compounds of formula X, where there are two occurrences of L, Z, and A: both groups L are absent or are the same; both groups Z are the same; and both anions A are the same.

Examples of such compounds include compounds of formulas XI and XII:

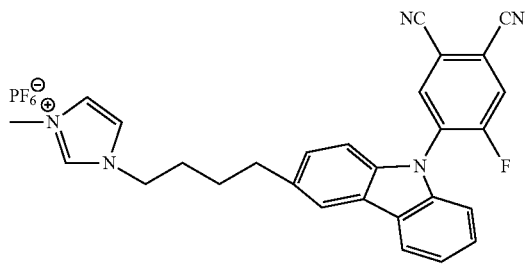

XI

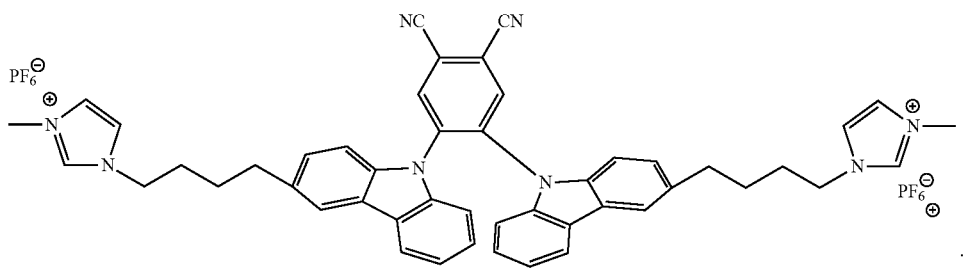

XII

In these complexes the linking groups L are:

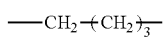

(1,4-butylene), the charged groups Z are:

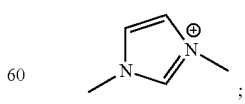

and the counter ions A are $PF_6^-$.

Compounds of formulas XI and XII have been shown to exhibit TADF behaviour and can be used in the fabrication of a LEEC as described in more detail hereafter.

As mentioned above cyano groups are used as substituents on cyanobenzene acceptor moieties in TADF species, typically with carbazole or related nitrogen containing species as donors. As an alternative to cyano substituents, charged groups such as carboxylate (—$CO_2^-$), sulfonate (—$SO_3^-$) phosphate (—$PO_4^-$), quaternary ammonium (—$NR_3^+$) or phosphonium (—$PR_3^+$) may be employed. This allows the charged substituents that facilitate use in a LEEC to be an integral part of the TADF species. It is also possible to have charged groups on both the acceptor and on the donor moieties of a TADF species. Suitable counter ions are used as appropriate.

As a yet further alternative charged groups may be provided by use of a carboxylic ester function —$CO_2$-L-Z on acceptor moieties. The carboxylic ester function provides acceptor behaviour to the acceptor moieties, L represents an optional linking group and Z a charged group. Both L and Z have the same meaning as discussed herein with respect to formulas II, III and IV.

Thus for example charged derivatives of compounds of formula V or XIII:

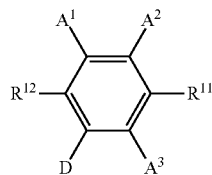

V

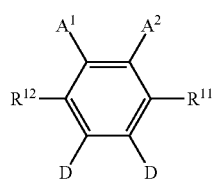

XIII wherein each of $A^1$, $A^2$, $A^3$ $R^{11}$, $R^{12}$ and D has, independently for each occurrence the same meaning as discussed above with respect to compounds of formula V may be employed together with sufficient suitable counter ions A to balance charge.

A further example of charged compounds in accordance with the invention is provided by charged derivatives of the compound XVI, where sulphone (—$SO_2$—) provides acceptor behaviour,

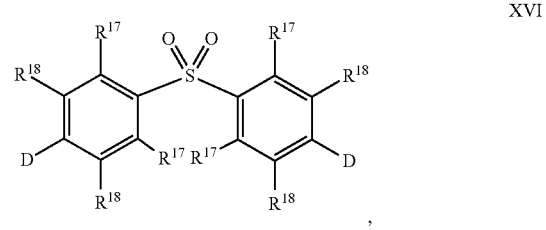

XVI wherein donor moieties D, independently for each occurrence take the same meaning as discussed above with respect to compounds of formula V; $R^{17}$ and $R^{18}$ independently for each occurrence take the same meaning as discussed above as substituents $R^{11}$ and $R^{12}$ in compounds of formula V; and at least one charged group Z is provided: each group Z being provided either directly or via a linking group L at one of the occurrences of $R^{17}$ and $R^{18}$ or attached to a donor moiety D; wherein each L if present and each Z has, independently for each occurrence, the same meanings as discussed above for compounds of formulas II, III or IV.

Examples of charged derivatives of formula XVI include charged derivatives of formula XVIa or XVIb

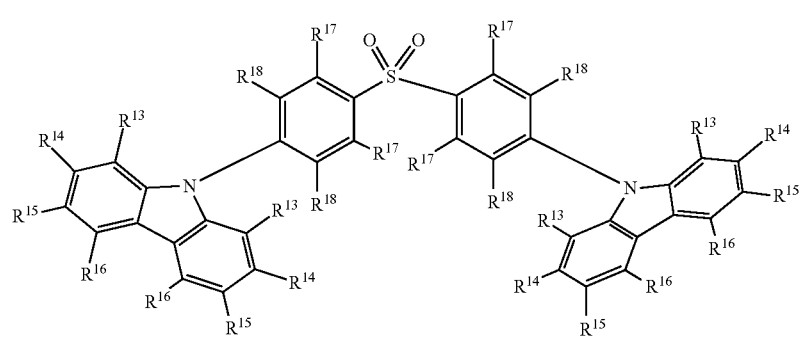

XVIa

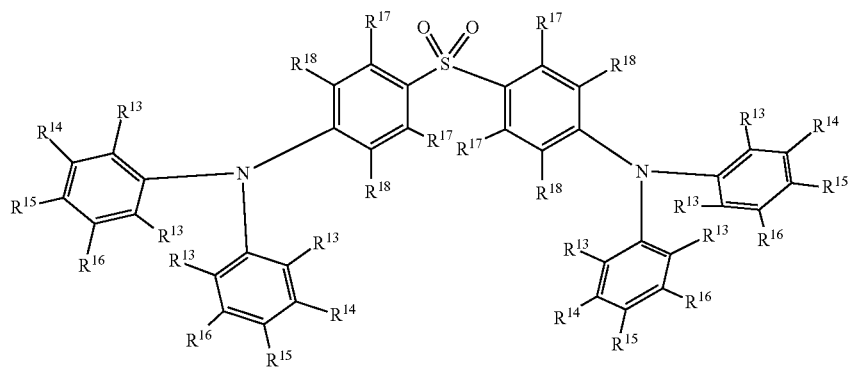

XVIb wherein at least one of the occurrences of $R^{13}$, $R^{14}$, $R^{15}$, $R^{16}$, $R^{17}$ and $R^{18}$ represents the bonding position, either directly or via a linking group L, to a charged group Z, each L if present and each Z having, independently for each occurrence, the same meanings as discussed above for compounds of formula III or IV; and wherein each group of $R^{13}$, $R^{14}$, $R^{15}$, $R^{17}$ and $R^{18}$ not involved in bonding to an organic charged group Z is, independently for each occurrence, selected from the group consisting of —H, substituted or unsubstituted primary, secondary or tertiary alkyl, that may be cyclic and may be unsaturated (for example C1-C10 or even C1-C4); substituted or unsubstituted aryl or heteroaryl, —CF$_3$, —OMe, —SF$_5$, —NO$_2$, halo (e.g. fluoro, chloro, bromo and iodo), aryl, aryl hydroxy, amino, alkoxy, alkylthio, carboxy, cyano, thio, formyl, ester, acyl, thioacyl, amido, sulfonamido, carbamate, phosphine oxide, phosphine sulphide and the like. Where the substituent is amino it may be NH$_2$, NHR or NR$_2$, where the substituents R on the nitrogen may be alkyl, aryl or heteroaryl (for example substituted or unsubstituted C1-C20 or even C1-C10).

Conveniently the TADF moieties according to formula XVIa or formula XVIb bond to a charged group Z, via at least one of the positions $R^{15}$ (para to the carbazole or diphenylamine nitrogen). Conveniently both carbazole or diphenylamine structures in the TADF moieties of formula XVIa or of formula XVIb have the same substitution pattern.

Thus the charged TADF moieties of formula XVIa or of formula XVIb may be according to formula XVIc or formula XVId:

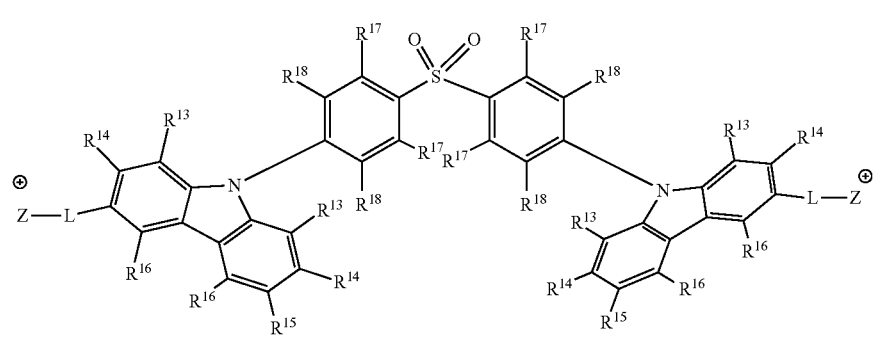

XVIc

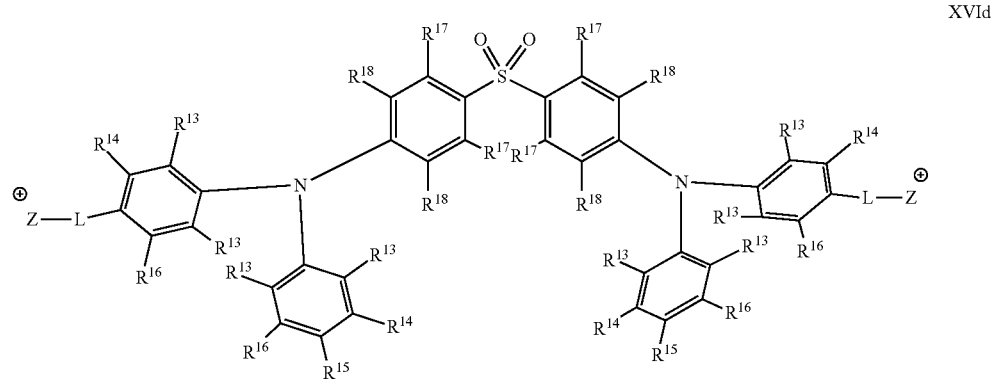

XVId wherein the groups Z are the charged groups bonded to the rest of the molecule by optional linkages L as described herein and each group of $R^{13}$, $R^{14}$, $R^{15}$, $R^{16}$, $R^{17}$ and $R^{18}$ depicted is not involved in bonding to an organic charged group Z.

All the groups R depicted may be H. Thus the charged TADF moieties of formula XVIc or formula XVId may be of formula XVIe or XVIf.

XVIe

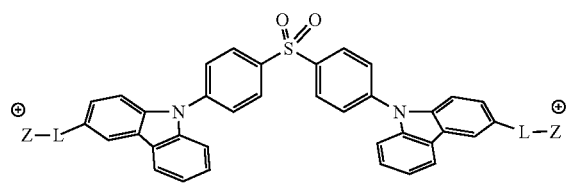

XVIf

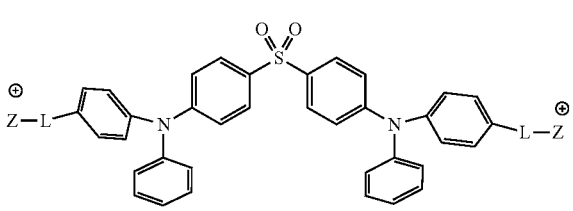

Examples of compounds of formula XVI include compounds of formula XVII and of formula XX:

XIIIa

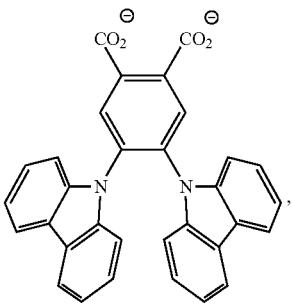

with cationic counter ion or counter ions A used to balance the charges. For example potassium ions.

Synthesis of charged organic thermally activated delayed fluorescence (TADF) species and sufficient counter ions to balance the charge on the charged organic thermally activated delayed fluorescence (TADF) species can be carried out by a skilled person. These salts may be made by modification of the TADF species to provide charged species and the desired counter ion or counter ions used in the synthetic route to the charged species or introduced by suitable ion exchange procedures.

XVII

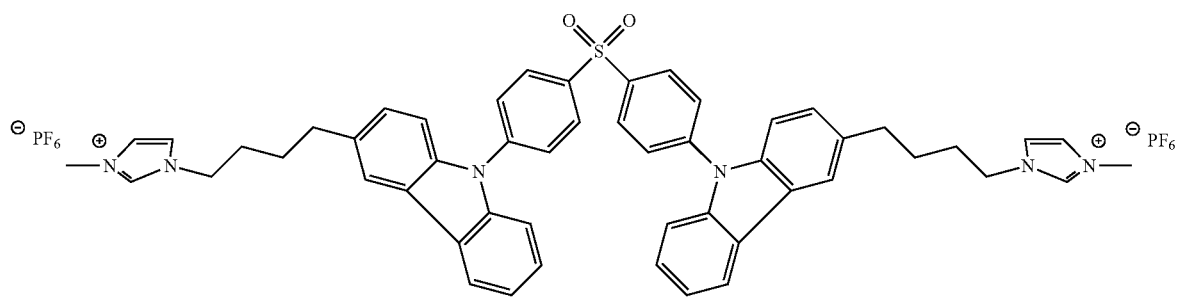

XX

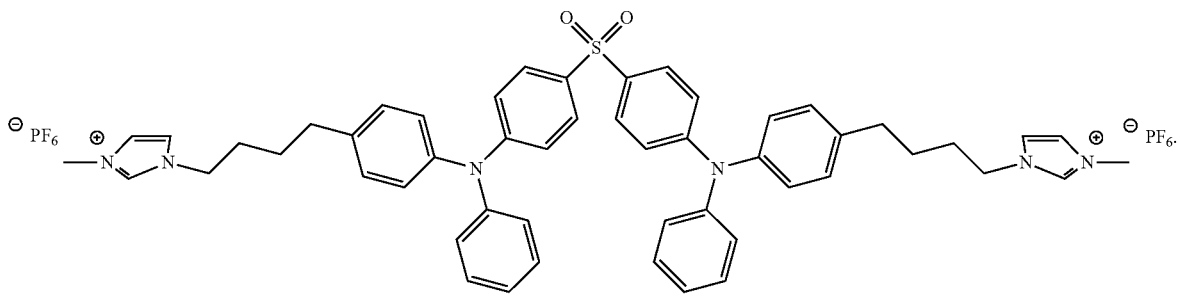

Compound XVII has carbazole donor moieties and compound XX has diphenylamine donor moieties.

An example where the charge is part of the TADF species is when $A^1$ and $A^2$, may be $-CO_2^-$ and groups D may be carbazole as in XIIIa:

For example, the cyano groups on dicyanobenzene acceptor moieties of TADF molecules may be modified to provide carboxylate, carboxylic acid, or carboxylic ester groups. For further example, carbazole or similar donor moieties of TADF molecules may be modified before and/or after synthesis of the TADF molecule to provide a charged group or groups.

Examples of compounds of the invention therefore include compounds of formulas XVIII, XIX, XXI, XXII and XXIII:

ions to balance the charge on the charged organic thermally activated delayed fluorescence (TADF) species as emitter material.

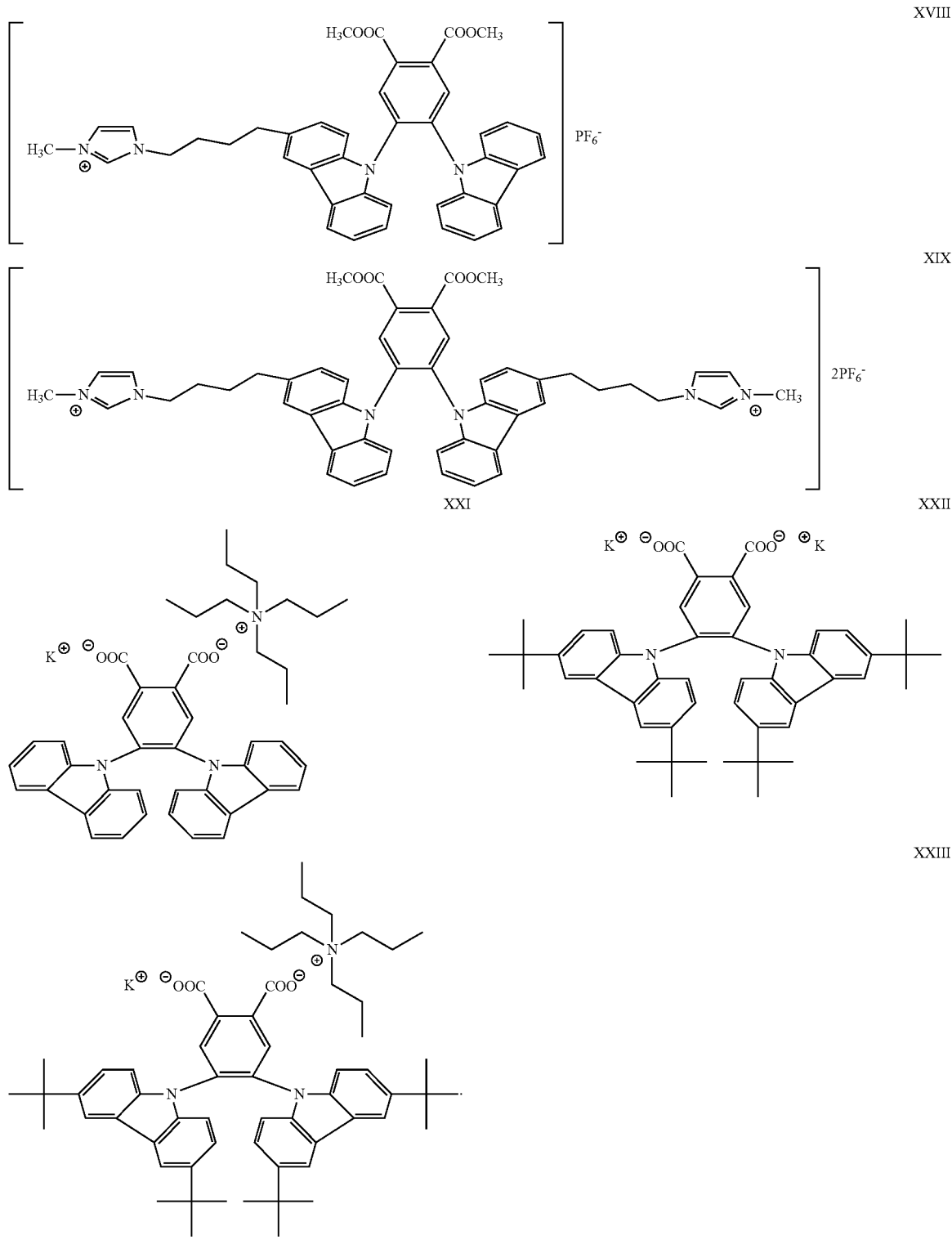

The light-emitting electrochemical cell (LEEC) of the invention uses a charged organic thermally activated delayed fluorescence (TADF) species and sufficient counter A typical LEEC of the invention may comprise two electrodes with a layer comprising the charged organic thermally activated delayed fluorescence (TADF) species and sufficient counter ions to balance the charge as the organic semiconductor layer that exhibits electroluminescence. The luminescent layer may consist of or consist essentially of the charged organic thermally activated delayed fluorescence (TADF) species and counter ions. However, as is known in the art ionic liquids such as 1-butyl-3-methylimidazolium hexafluorophosphate [Bmim][$PF_6$] may be employed to provide further ions. Other options include a host guest system where the electroluminescent material is dispersed in a matrix. For example a matrix of a charged organic material.

According to a further aspect the present invention provides a compound according to formula V:

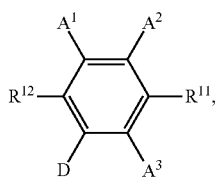

V wherein D, $R^{11}$, $R^{12}$, $A^1$, $A^2$, and $A^3$ have the same meaning as discussed above, and with suitable counter ions to balance the charges on group(s) Z. and/or groups $A^1$, $A^2$, and $A^3$ if they carry charges. When not being used as emitter material in a LEEC then the compound of formula V may be provided without charged groups Z and corresponding counter ions (and optional linking groups L), even if none of $A^1$, $A^2$, and $A^3$, are charged. As compounds of formula V are TADF molecules they may be used in light emitting devices such as OLEDs, when charged or when not charged. Thus the invention includes a light emitting device for example an Organic Light Emitting Diode, comprising a compound of formula V.

Thus the invention provides a compound according to formula XIV:

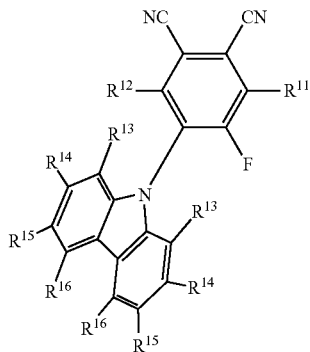

XIV wherein each group $R^{11}$, $R^{12}$, $R^{13}$, $R^{14}$, $R^{15}$ and $R^{16}$ is, independently for each occurrence, selected from the group consisting of —H, substituted or unsubstituted primary, secondary or tertiary alkyl, that may be cyclic and may be unsaturated (for example C1-C10 or even C1-C4); substituted or unsubstituted aryl or heteroaryl, —$CF_3$, —OMe, —$SF_5$, —$NO_2$, halo (e.g. fluoro, chloro, bromo and iodo), aryl, aryl hydroxy, amino, alkoxy, alkylthio, carboxy, cyano, thio, formyl, ester, acyl, thioacyl, amido, sulfonamido, carbamate, phosphine oxide, phosphine sulphide and the like. Where the substituent is amino it may be $NH_2$, NHR or $NR_2$, where the substituents R on the nitrogen may be alkyl, aryl or heteroaryl (for example substituted or unsubstituted C1-C20 or even C1-C10).

Compounds of formula XIV exhibit good TADF behaviour and can be used for devices such as OLEDs. Thus the invention also includes a light emitting device for example an Organic Light Emitting Diode, comprising a compound of formula XIV.

For example the compound of formula XIV may be in accordance with formula XV:

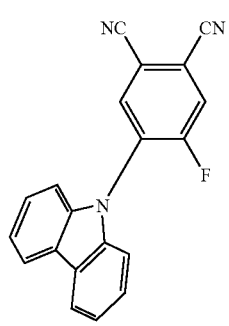

XV

According to a further aspect the present invention provides a compound of formula XIIIc:

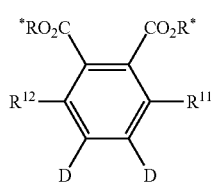

XIIIc wherein R* of acceptor groups, —$CO_2$R* are independently for each occurrence selected from H, alkyl, aryl or heteroaryl (for example substituted or unsubstituted C1-C20 or even C1-C10); and —$CO_2$-L-Z wherein L is an optional linking group and Z a charged group, each L if present and each Z having, independently for each occurrence, the same meanings as discussed above for compounds of formulas II, III or IV; and $R^{11}$, $R^{12}$ and D have, independently for each occurrence the same meaning as discussed above with respect to compounds of formula V, whether charged or uncharged.

For example R* may be alkyl or H.

When at least one charged group Z is present the compound according to formula XIIIc has suitable counter ions to balance the charges. Alternatively the compound according to formula XIIIc may be uncharged.

As compounds of formula XIIIc are TADF molecules they may be used in light emitting devices such as OLEDs, when charged or when not charged. Thus the invention includes a light emitting device for example an Organic Light Emitting Diode, comprising a compound of formula XIIIc.

Thus for example compounds of formula XIIIc, may take the form of formula XXIV:

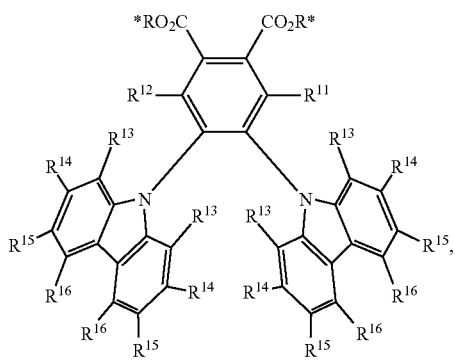

wherein R* of acceptor groups, —CO$_2$R* are independently for each occurrence selected from —H, alkyl, aryl or heteroaryl (for example substituted or unsubstituted C1-C20 or even C1-C10) and —CO$_2$-L-Z wherein L is an optional linking group and Z a charged group, each L if present and each Z having, independently for each occurrence, the same meanings as discussed above for compounds of formulas II, III or IV; and the donor moieties are carbazole derivatives as described above with respect to formula VI.

Alternatively none of the substituents R*, $R^{11}$, $R^{12}$, $R^{13}$, $R^{14}$, $R^{15}$ and $R^{16}$ may carry a charged group Z. The compound is neutral and so R* is selected from the group consisting of —H, alkyl, aryl or heteroaryl (for example substituted or unsubstituted C1-C20 or even C1-C10); and each $R^{11}$, $R^{12}$, $R^{13}$, $R^{14}$, $R^{15}$ and $R^{16}$ may be selected from the group consisting of: of —H, substituted or unsubstituted primary, secondary or tertiary alkyl, that may be cyclic and may be unsaturated (for example C1-C10 or even C1-C4); substituted or unsubstituted aryl or heteroaryl, —CF$_3$, —OMe, —SF$_5$, —NO$_2$, halo (e.g. fluoro, chloro, bromo and iodo), aryl, aryl hydroxy, amino, alkoxy, alkylthio, carboxy, cyano, thio, formyl, ester, acyl, thioacyl, amido, sulfonamido, carbamate, phosphine oxide, phosphine sulphide and the like.

Where the substituent is amino it may be NH$_2$, NHR or NR$_2$, where the substituents R on the nitrogen may be alkyl, aryl or heteroaryl (for example substituted or unsubstituted C1-C20 or even C1-C10).

An example of a compound of formula XXIV that carries charge at both the carboxylic acceptor groups and the donor moieties is formula XXV:

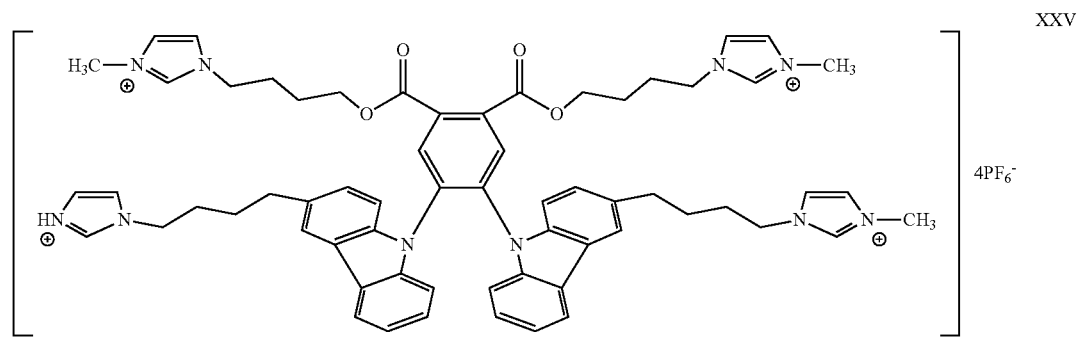

whose synthesis is described hereafter.

DETAILED DESCRIPTION OF SOME EMBODIMENTS AND EXPERIMENTAL RESULTS

Synthesis of Compounds

Figure 1:
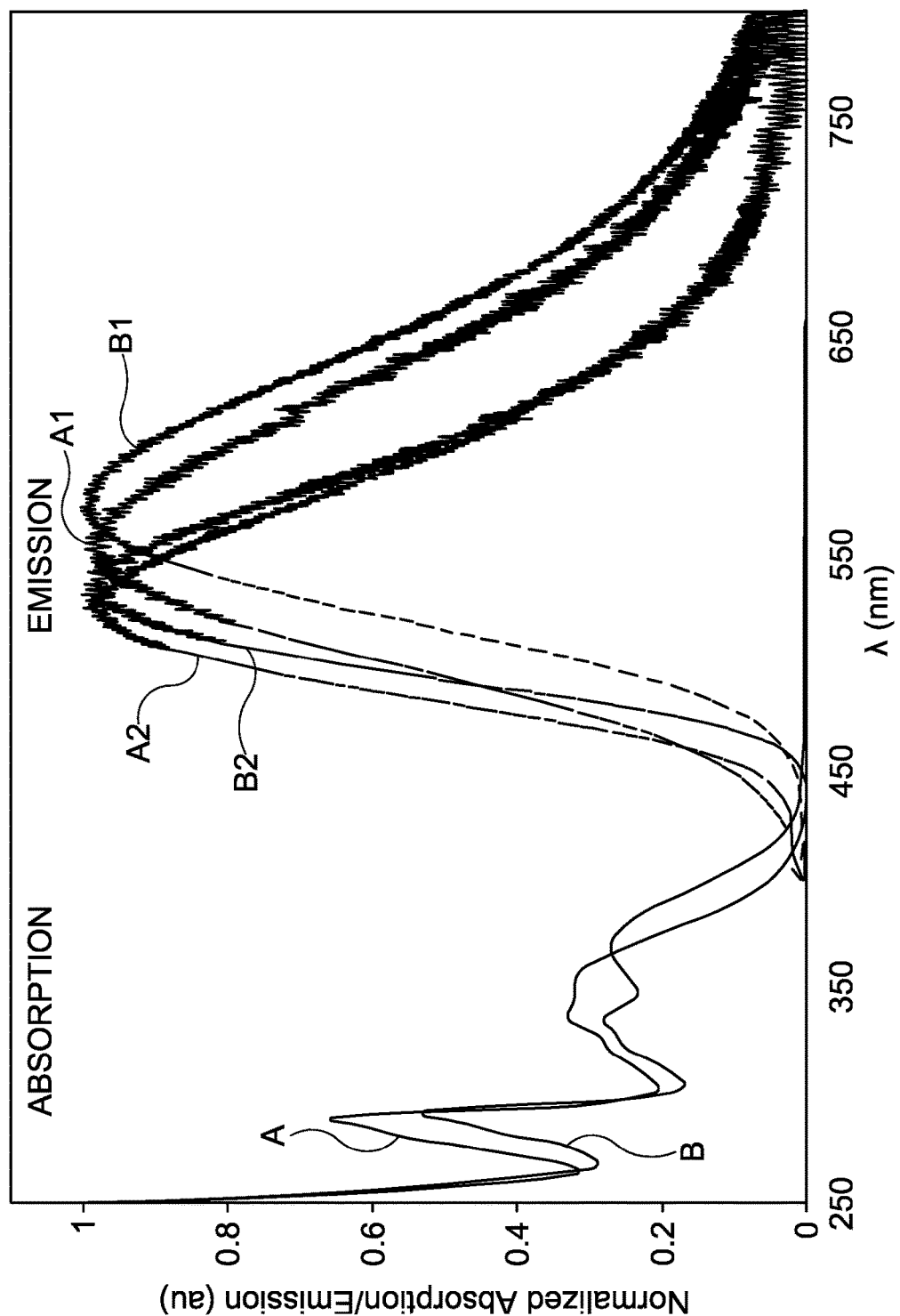
FIG. 1 shows absorption and emission spectra of TADF compounds.

Synthesis of compounds of formulas XI and XII is illustrated in Scheme 1 below. A similar procedure may be employed when making TADF species incorporation donor moieties other than modified carbazole species.

Scheme 1.
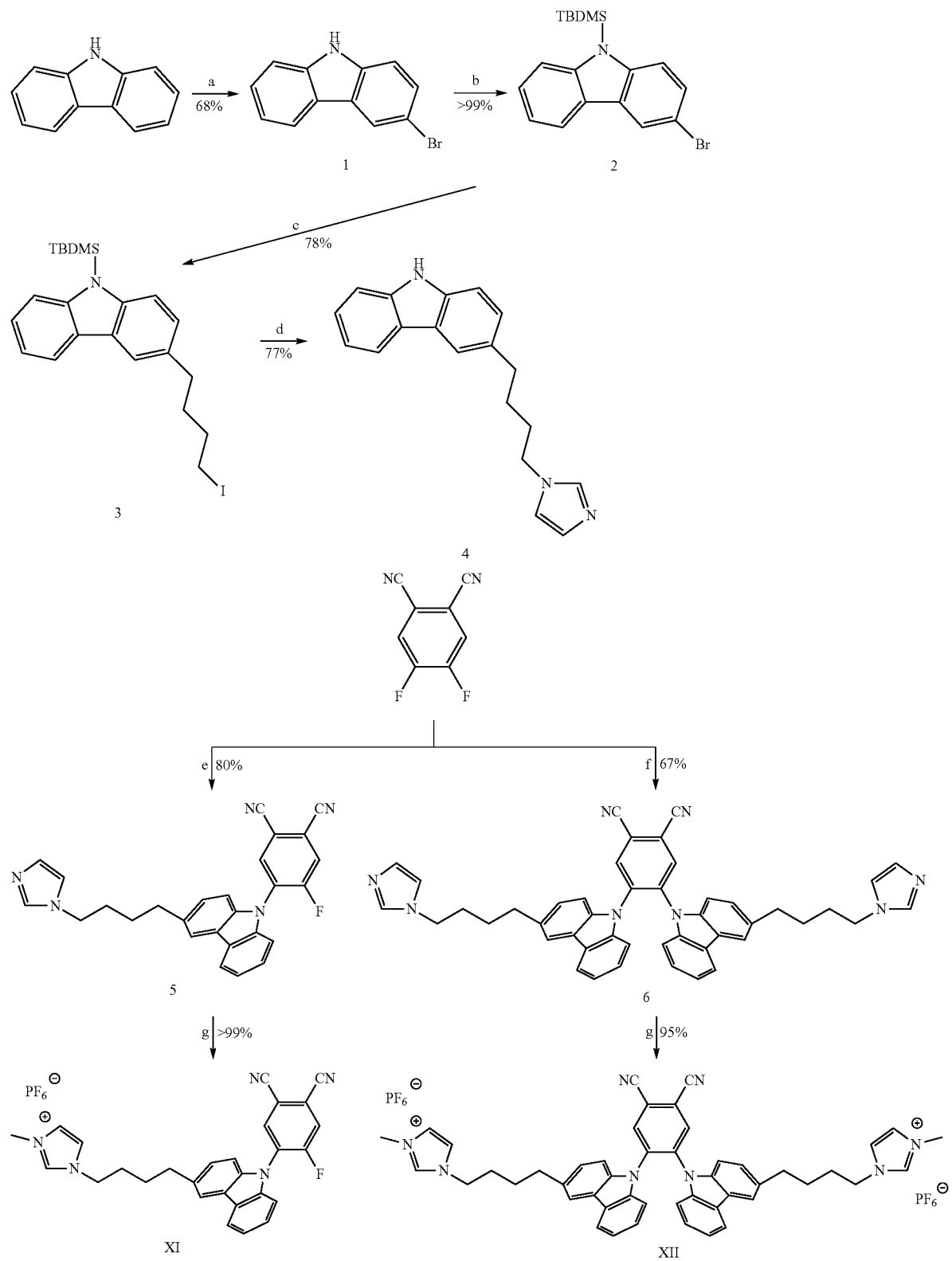
Synthesis of the charged TADF emitters for LEEC XI and XII. a. NBS, ACN, rt, 1 h. b. i) NaH, THF, rt, 30 min, ii) TBDMSiCl c. i) n-BuLi, THF, -78° C., 30 min, ii) excess 1,4-diiodobutane. d. NaH, imidazole, THF, reflux, 4 h. e. i) NaH, 4, THF, rt, 30 min, ii) 2 equiv. 4,5-difluorophthalonitrile, rt, 4 h. f. i) NaH, 4, THF, rt 30 min, ii) 0.6 equiv. 4,5-difluorophthalonitrile, rt, 4 h. g. i) MeI, ACN, 40° C., 2 h ii) sat. $NH_4PF_6$ (aq).

In the procedures shown in Scheme 1, the preparation of 3-bromocarbazole 1 using N-bromosuccinimide was contaminated by some starting material and 3,6-dibromocarbazole, both of which could be removed by fractional recrystallization from toluene. The preparation of 3 was accomplished in good yield by dropwise introduction of the lithiated TBDMS-protected 3-bromocarbazole 2 intermediate to excess 1,4-diiodobutane.

Compound 4 was obtained by $S_N2$ reaction of sodium imidazolate with 3 followed by silyl deprotection using sodium hydride in a one-pot fashion.

Compounds 5 and 6 were synthesized by reacting 4 with sub-stoichiometric or stoichiometric 4,5-difluorophthalonitrile, respectively, under basic conditions via nucleophilic aromatic substitution reaction. The targeted charged TADF emitters XI and XII were obtained following methylation with iodomethane and anion metathesis with saturated $NH_4PF_6$ solution in 33% and 27% yield, respectively, over six steps. The solubilities of XI and XII in DCM were greatly improved after the anion metathesis, in comparison with that of the original iodo salts.

Both XI and XII exhibit irreversible oxidation and reversible oxidation waves in MeCN solution by cyclic voltammetry.

The HOMO of XI (−5.93 eV) is slightly lower than that of XII (−5.87 eV) due to the presence of electron-withdrawing fluorine atom. The LUMO of XI (−2.92 eV) is slightly higher than that of XII (−2.99 eV), which is due to the increased conjugation imparted by the second carbazole moiety that lowers the LUMO in XII. These structure-property relationships are mirrored in the absorption spectra wherein the absorption profile of XII is slightly red-shifted compared with in XI (See FIG. 1).

In FIG. 1 the normalised absorption spectra in aerated acetonitrile for XI (line A) and XII (line B) are shown—at 298K. Also shown are the corresponding emission spectra for XI in deaerated acetonitrile (line A1) and thin film (line A2). Also shown are the corresponding emission spectra for XII in deaerated acetonitrile (line B1) and thin film (line B2).

The electrochemical and emission data for XI and XII are summarised in Table 1 below. $\lambda_{em}$ is the wavelength of maximum emission, $\phi$ is the photo luminescence quantum yield, $\tau_e$ is the fluorescence lifetime, $E_{HOMO}$ and $E_{LUMO}$ are the energy levels obtained from cyclic voltammetry with $\Delta E$ being the difference.

TABLE 1

Emission and electrochemical data of the TADF-LEEC dyes XI and XII.

| Dye | | Emission | | | Electrochemical | | |
|---|---|---|---|---|---|---|---|
| | | $\lambda_{em}$ (nm)[a] | $\phi$ (%)[b] | $\tau_e$ (ns)[c] | $E_{HOMO}$[e] (eV) | $E_{LUMO}$[e] (eV) | $\Delta E$ (eV) |
| XI | Aerated | 556 | 1.4 | 2.90 | −5.93 | −2.92 | 3.01 |
| | Degassed | 558 | 2.9 | 3.26 | | | |
| | Thin Film | 526 | 9.1[d] | 42.9 (83.4%), 4580 (16.6%) | | | |
| XII | Aerated | 574 | 2.1 | 4.44 | −5.87 | −2.99 | 2.88 |
| | Degassed | 572 | 2.6 | 4.97 | | | |
| | Thin Film | 536 | 35.5[d] | 35.2 (80.6%), 11700 (19.4%) | | | |

[a]Measured at 298 K; $\lambda_{exc}$: 360 nm.
[b]Quinine sulfate used as the reference ($\phi_{PL}$ = 54.6% in in 1N $H_2SO_4$ at 298 K). $\lambda_{exc}$: 378 nm.
[d]Measured using an integrating sphere at 298 K in ambient air.
[e]The HOMO and LUMO energies were calculated using the relation $E_{HOMO/LUMO}$ = $-(E^{ox}_{pa}, 1/E^{red}_{1/2} + 4.8)$ eV, where $E^{ox}_{pa}, 1/E^{red}_{1/2}$ are the oxidation and reduction peaks, respectively referenced vs Fc/Fc+.

The emission in MeCN solution and in a thin solid film for both in XI and XII is broad and unstructured, characteristic of CT (charge transfer) emission; the excitation and absorption spectra matched, pointing to a high level of purity. The emission spectra in MeCN are red-shifted by about 30-40 nm, respectively, compared to emission in the thin film. The thin film was deposited from a solution of acetonitrile in a film without any dopants or other additives present.

In solution, the emission for both XI and XII is weak and the observed lifetimes are in the nanosecond regime. There is little change in the photophysical properties upon degassing the sample, suggesting that in MeCN XI and XII act as fluorophores with no observed TADF. This is likely due to stronger stabilization of the triplet state by the solvent resulting in increased $\Delta E_{ST}$. By point of comparison, dicarbazolyldicyanobenzene was shown by Adachi to emit at 473 nm in toluene solution via TADF with a photoluminescence quantum yield, $\Phi_{PL}$, of 47% (reference 1a). In the neat film, XI and XII are much brighter with $\Phi_{PL}$ values of 9.1 and 35.5%, respectively, under aerated conditions. Importantly, biexponential decay in the emission lifetimes is now observed, including both a short component and a long microsecond component, a hallmark of TADF emission.

Synthesis of compound of formula XVII is illustrated in Scheme 2 below and follows a similar route to that of Scheme 1.

Reaction of compound 4 from Scheme 1 above with bis(4-fluorophenyl) sulphone provides the intermediate 7 which is converted by methylation with iodomethane and anion metathesis with saturated $NH_4PF_6$ solution to the product XVII.

Scheme 2

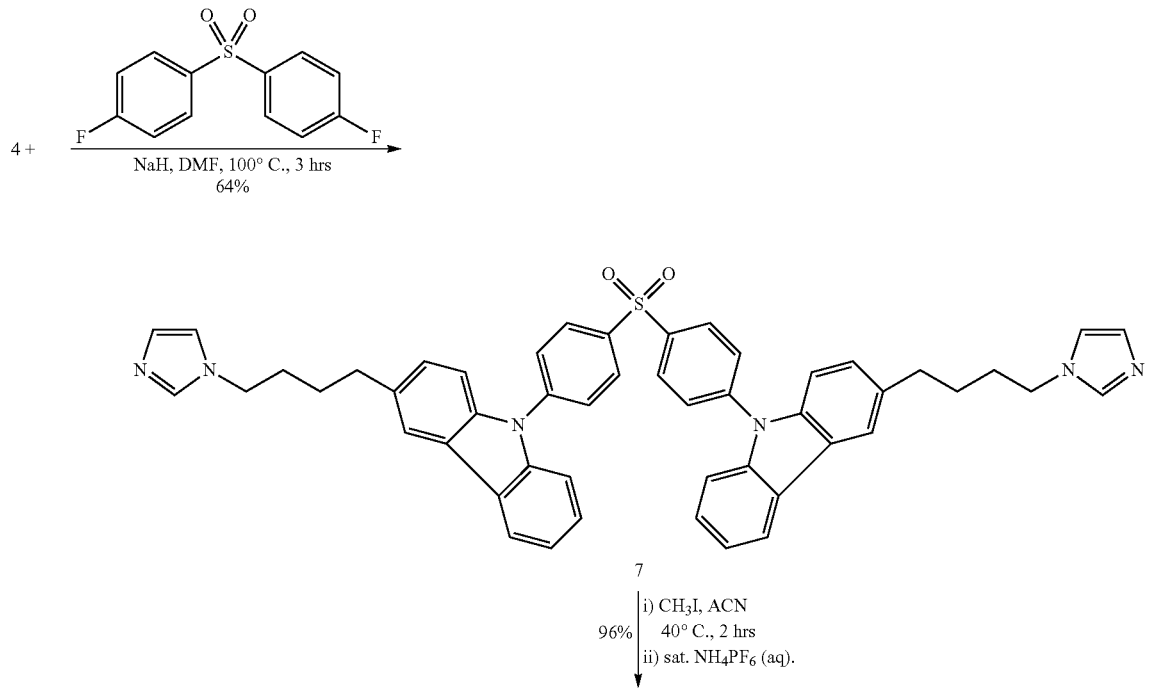

i) CH₃I, ACN
40° C., 2 hrs
96%
ii) sat. NH₄PF₆ (aq).

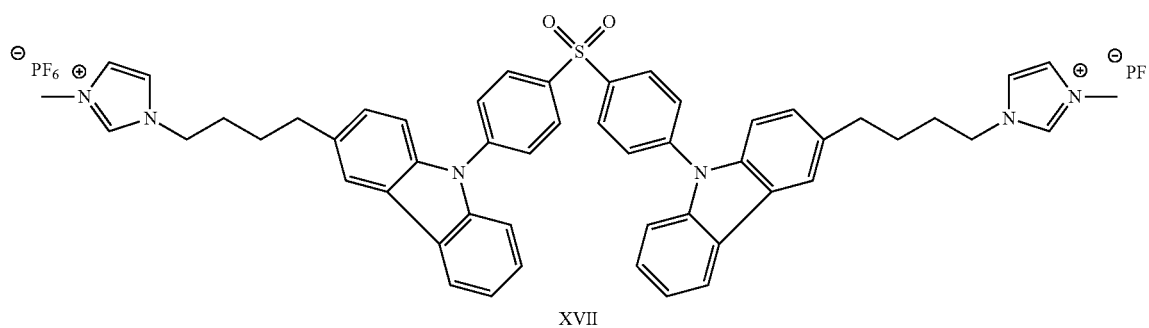

Synthesis of compound of formula XVIII is illustrated in Scheme 3 below.

Reaction of 0.5 molar equivalents of carbazole with 4,5-difluorophthalonitrile affords compound 8 which is then reacted with 4 to provide intermediate 9. Hydrolysis of the nitrile functions provides dicarboxylic acid 10 on acidification. Methylation with iodomethane and anion metathesis with saturated NH₄PF₆ solution provides the product XVIII.

Scheme 3

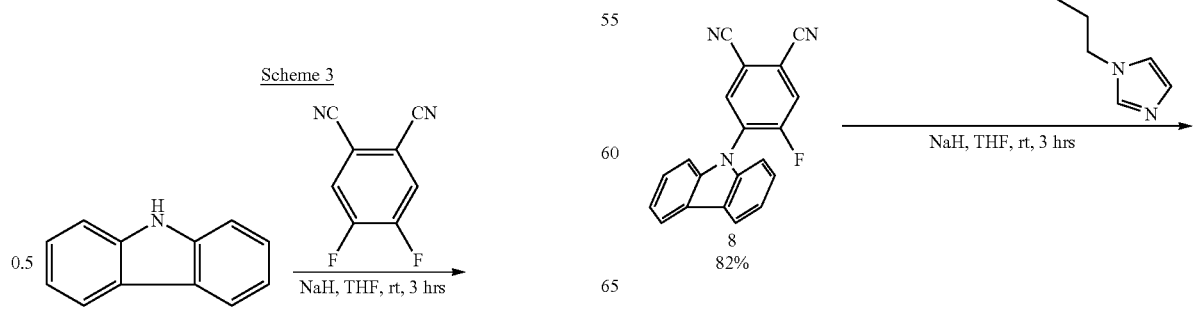

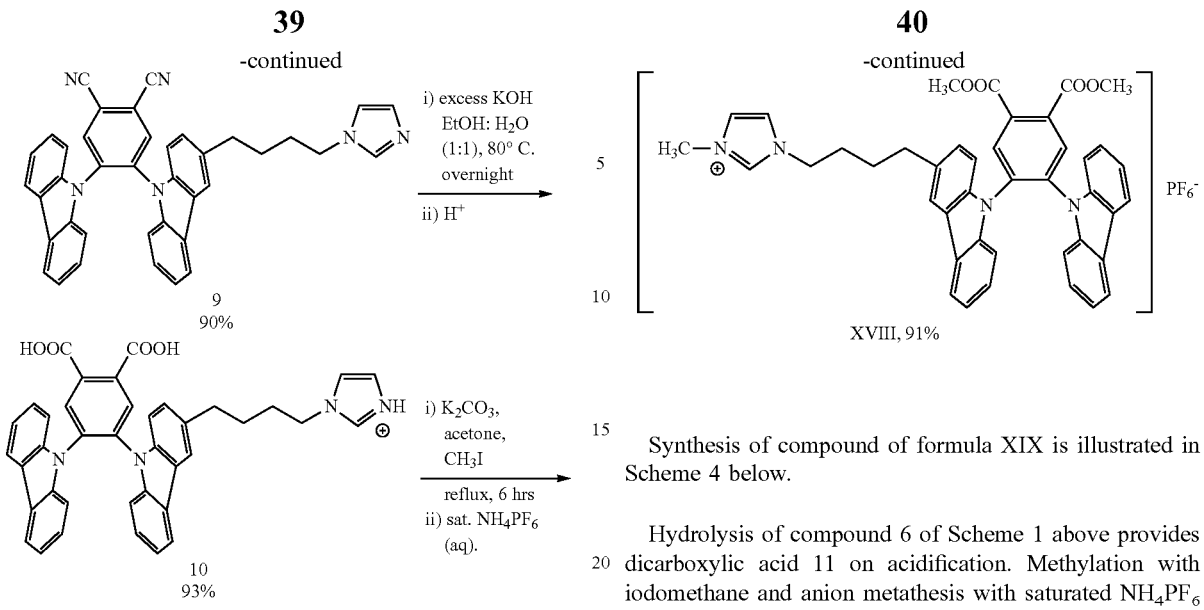
Synthesis of compound of formula XIX is illustrated in Scheme 4 below.
Hydrolysis of compound 6 of Scheme 1 above provides dicarboxylic acid 11 on acidification. Methylation with iodomethane and anion metathesis with saturated $NH_4PF_6$ solution provides the product XIX.
Scheme 4
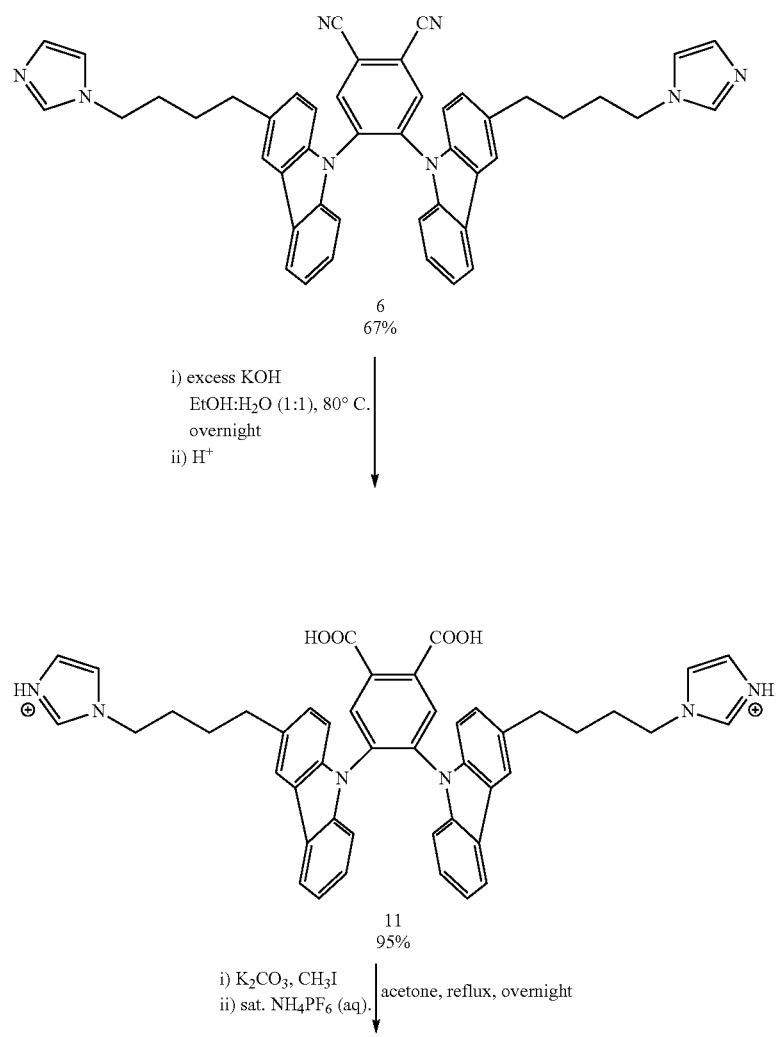

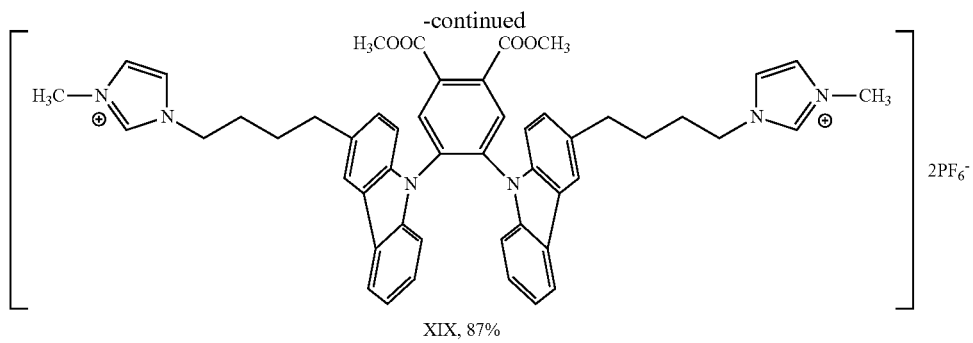

XIX, 87%

Synthesis of compound of formula XX is illustrated in Scheme 5 below.

Diphenylamine 12 is converted to the imidazole derivative 13 by a similar route to that shown for carbazole in Scheme 1 above. Reaction of 13 with bis(4-fluorophenyl) sulphone affords intermediate 14. Methylation with iodomethane and anion metathesis with saturated $NH_4PF_6$ solution provides the product XX.

Scheme 5

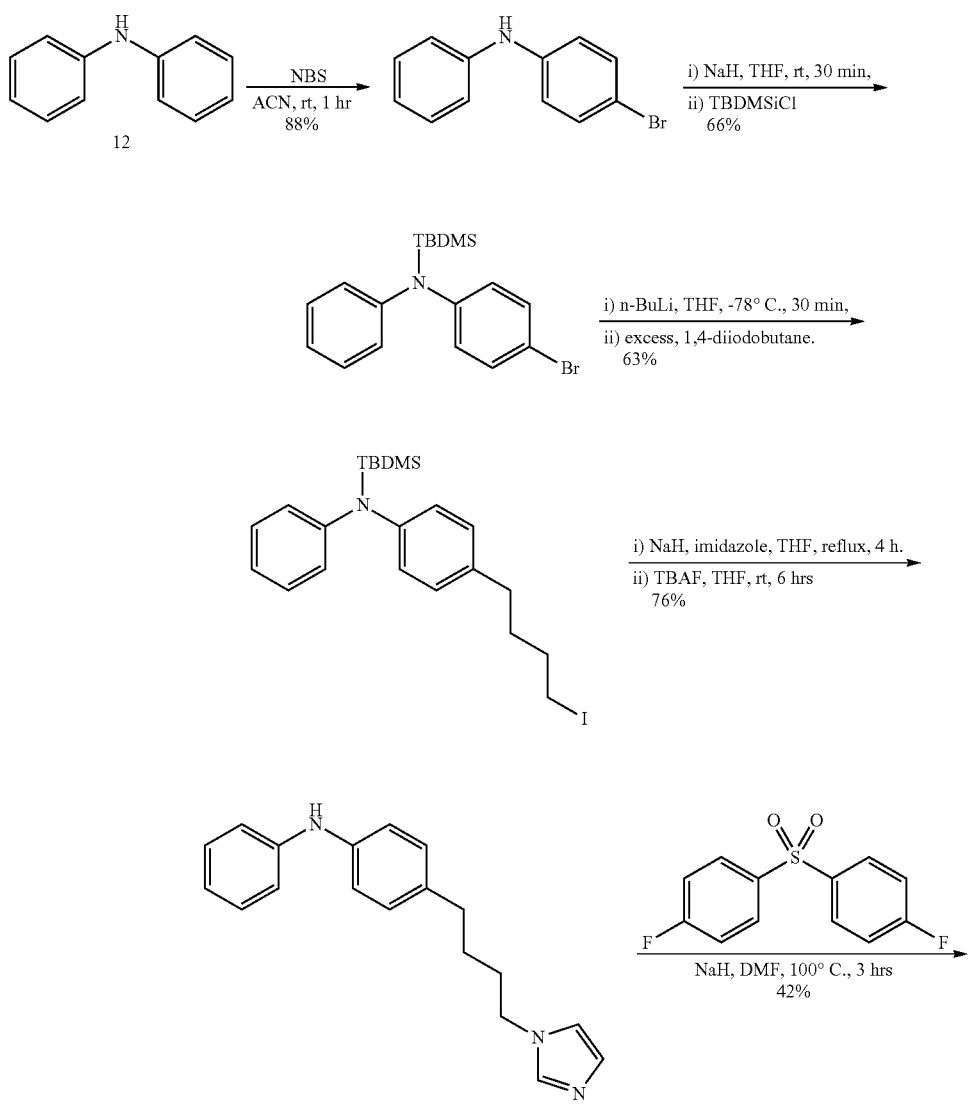

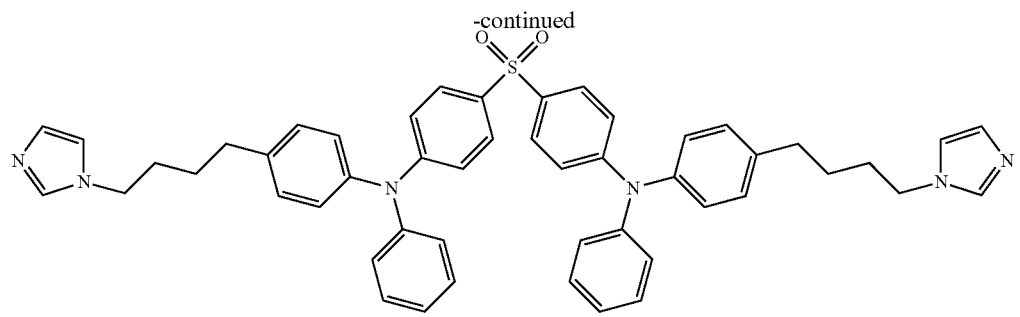

14

93% | i) CH₃I, ACN
ii) sat. NH₄PF₆ (aq).
40° C., 2 hrs

XX

Syntheses of compounds of formulas XXI, XXII and XXIII are illustrated in Scheme 6 below.

Reaction of carbazole with 4,5-difluorophthalonitrile affords intermediate 15 which on hydrolysis provides potassium salt of the dicarboxylic acid 16. Reaction with n-Pr₄NBr affords the product XXI. A similar approach using 3,6-di-tert-butyl-9H-carbazole 17 affords the intermediate 18 on reaction with 4,5-difluorophthalonitrile. Hydrolysis provides the potassium salt of the dicarboxylic acid XXII. Conversion to the product XXIII is made by reaction with n-Pr₄NBr.

Scheme 6

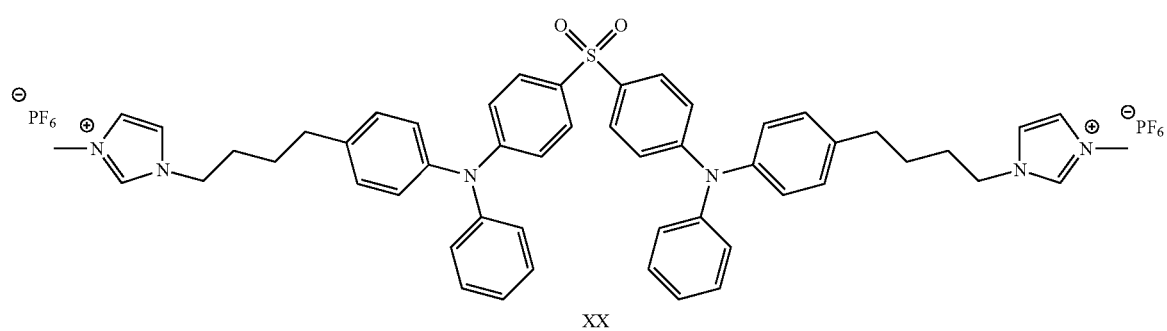

17

NaH, THF, rt, 3 hrs

-continued
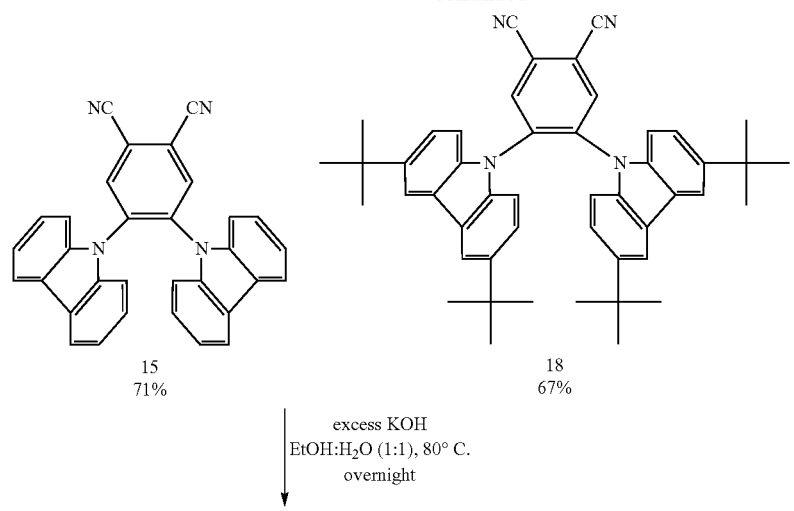
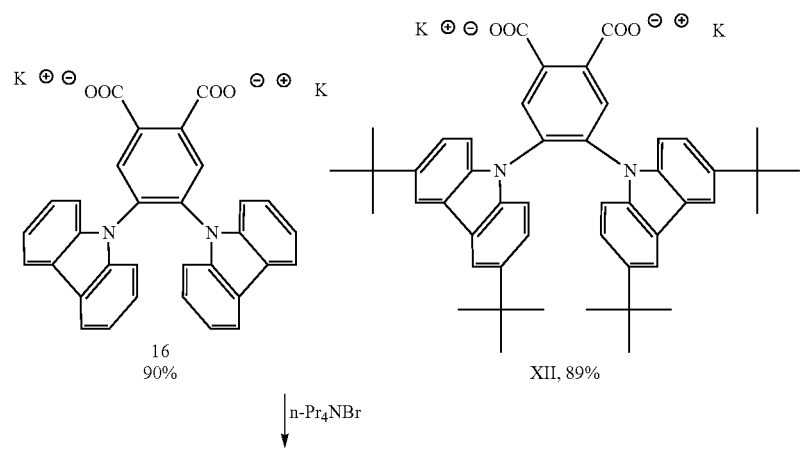
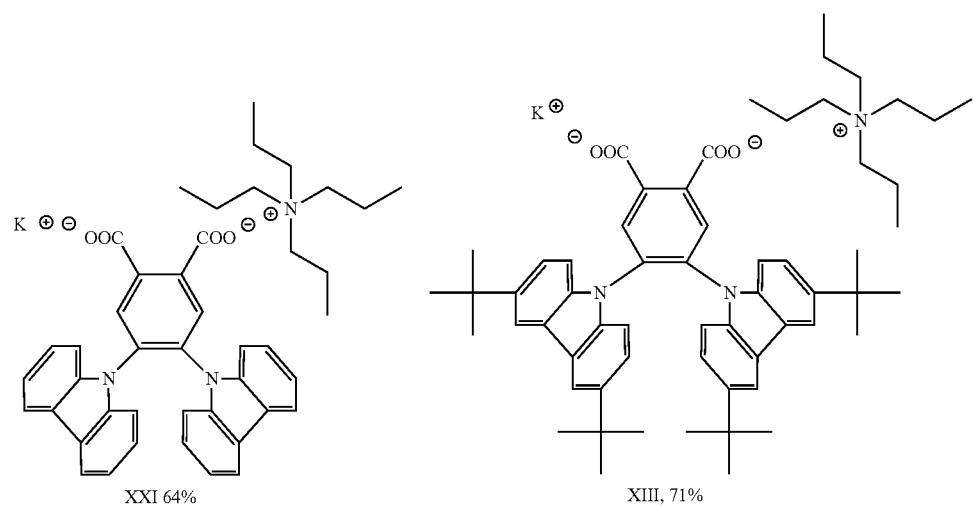

Synthesis of compound of formulas XXV is illustrated in Scheme 7 below.
Reaction of imidazole with 1,4-dibromobutane affords 19 which on reaction with 11 (see Scheme 4) provides di-ester 20.
Methylation with iodomethane and anion metathesis with saturated NH$_4$PF$_6$ solution provides the product XXV.
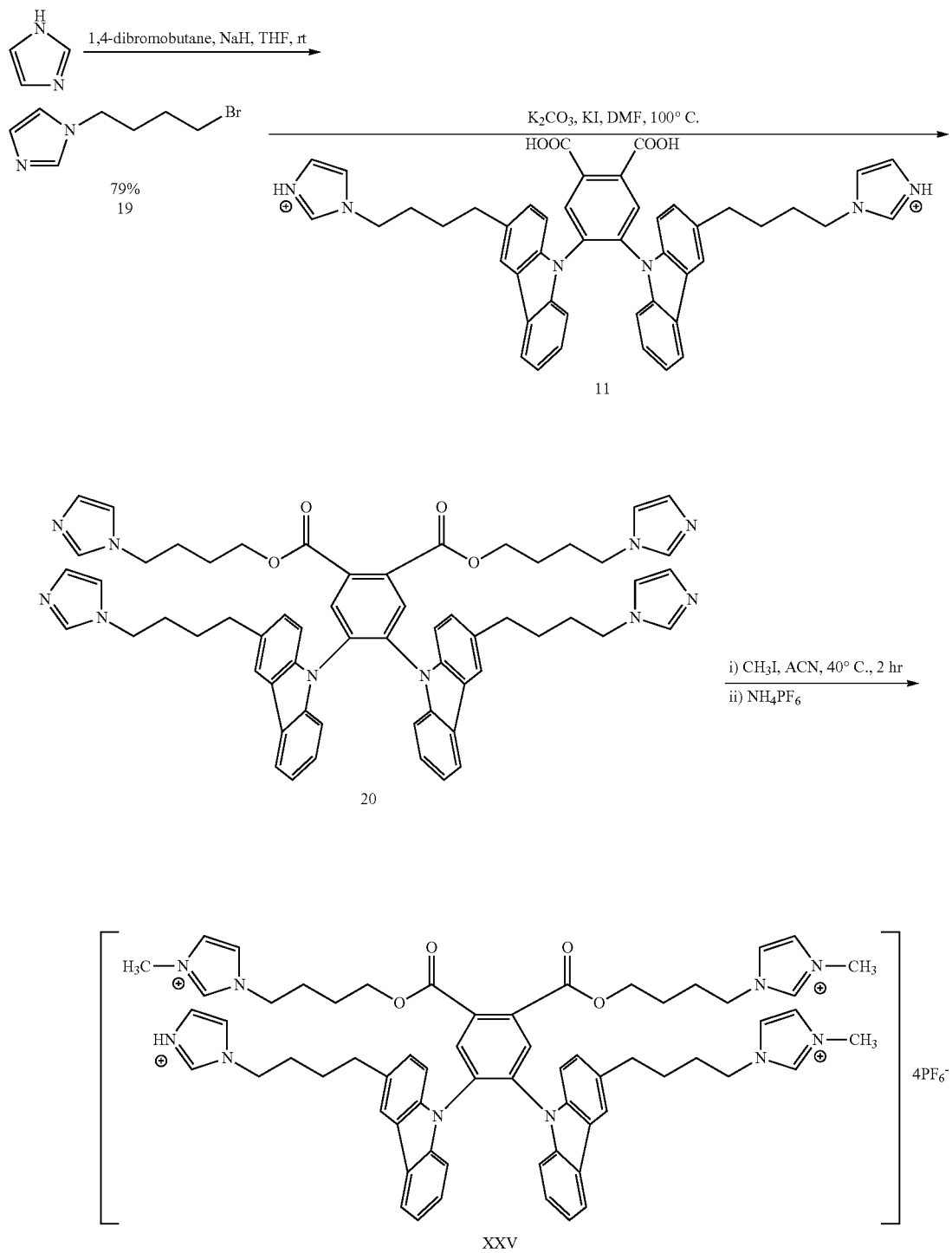
Scheme 7

Emission and electrochemical data of the TADF-LEEC dyes XIII to XXIV are shown in Table 2 below.

TABLE 2

| Com-pound | Solution[a] $\lambda_{em}$[c] (nm) | $\phi_{PL}$[d] (%) | $\tau_e$ (ns) | Doped Film[b] $\lambda_{em}$ (nm) | $\phi_{PL}$ (%) | Electro-chemistry[e] (eV) |
|---|---|---|---|---|---|---|
| XVII | 439 (81) | 45.5 (30.2) | 11.5, 821 | 440 (78) | 44.1 (46.1) | HOMO: −5.65 LUMO: −2.08 ΔE: 3.57 |
| XX | 447 (81) | 46.7 (45.0) | 6.7, 684 | 416 (70) | 49.3 (48.3) | N/A |
| XVIII | 509 (120) | 22.1 (18.2) | 21.0, 2490 | 462 (109) | 50.6 (37.4) | HOMO: −5.88 LUMO: −2.66 ΔE: 3.22 |
| XIX | 515 (126) | 19.5 (12.7) | 17.7, 1770 | 494 (122) | 35.8 (32.1) | HOMO: −5.91 LUMO: −2.65 ΔE: 3.26 |
| XXIV | | | | N/A | | |
| XXI | 441 (86) | 51.4 (41.2) | 16.6, 600 | 424 (90) | 16.5 (19.5) | HOMO: −5.74 LUMO: N/A ΔE: N/A |
| XXII | 455 (125) | 33.6 (11.5) | 17.0, 4470 | 462 (111) | 40.4 (36.5) | HOMO: −5.85 LUMO: N/A ΔE: N/A |
| XXIII | 465 (96) | 32.8 (27.8) | 19.0, 1420 | 430 (96) | 29.0 (23.7) | HOMO: −5.93 LUMO: N/A ΔE: N/A |

[a]In DCM at 298 K.
[b]Doped with PMMA (10 wt %) and spin-coated.
[c]Emission maxima and full-width at half maximum (FWHM) are reported from degassed solutions. FWHM in parentheses.
[d]0.5M quinine sulphate in $H_2SO_4$ (aq) was used as reference (PLQY: 54.6%). Values quoted are in degassed solutions, which were prepared by five freeze-pump-thaw cycles. Values in parentheses are for aerated solutions, which were prepared by bubbling with air for 5 minutes.
[e]In MeCN with 0.1M [nBu$_4$N]PF$_6$ as the supporting electrolyte and Fc/Fc$^+$ as the internal reference. The HOMO and LUMO energies were calculated using the relation $E_{HOMO/LUMO} = -(E^{ox}_{pa}, 1/E^{red}_{pc}, 1 + 4.8)$eV, where $E^{ox}_{pa}$ and $E^{red}_{pc}$ are anodic and cathodic peak potentials respectively.
$\Delta E = -(E_{HOMO} - E_{LUMO})$.
N/A = not available.

Fabrication of a LEEC

The compounds of the invention can be utilised in the fabrication of a LEEC.

In general LEECs were prepared on top of a patterned indium tin oxide (ITO) coated glass substrate. Prior to the deposition of the emitting layer, a 80 nm of PEDOT:PSS was coated in order to increase the reproducibility of the cells.

For XII the emitting layer (100 nm) was prepared by spin-coating of an acetonitrile solution consisting of the emitting compound alone or with the addition of an ionic liquid (IL) 1-butyl-3-methylimidazolium hexafluorophosphate [Bmim][PF$_6$] at a molar ratio of 4:1. After the deposition of the light-emitting layer the devices were transferred into an inert atmosphere glovebox. To complete the devices, a layer of 70 nm of aluminium that serves as the top electrode was thermally evaporated in a high vacuum chamber integrated in the inert atmosphere glovebox.

For XI a host guest matrix was employed as that salt did not produce light when in a pristine (additive free) solid film layer. Spin coating with the ionic host produced a functioning LEEC.

Compound XI was successfully fabricated into a LEEC with the compound prepared in a matrix of the known ionic host NS25, described in EP2733188 (which is incorporated by reference herein).

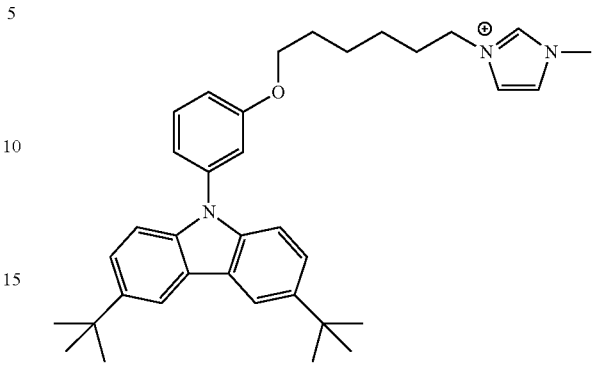

NS25

In order to determine the performance of the LEECs, the devices were operated using a block-wave pulsed current driving method (1000 Hz and 50% of duty cycle) at different average current densities of 10, 25 and 50 Am$^{-2}$. This operational mode was selected over constant voltage mode as it decreases the turn-on time and leads to a more sustained behaviour versus time.

The luminance and average voltage are depicted in FIG. 2 for LEECs using XII and XII: [Bmim][PF$_6$] 4:1 mixture as the component(s) for the light-emitting layer.

Figure 2A:
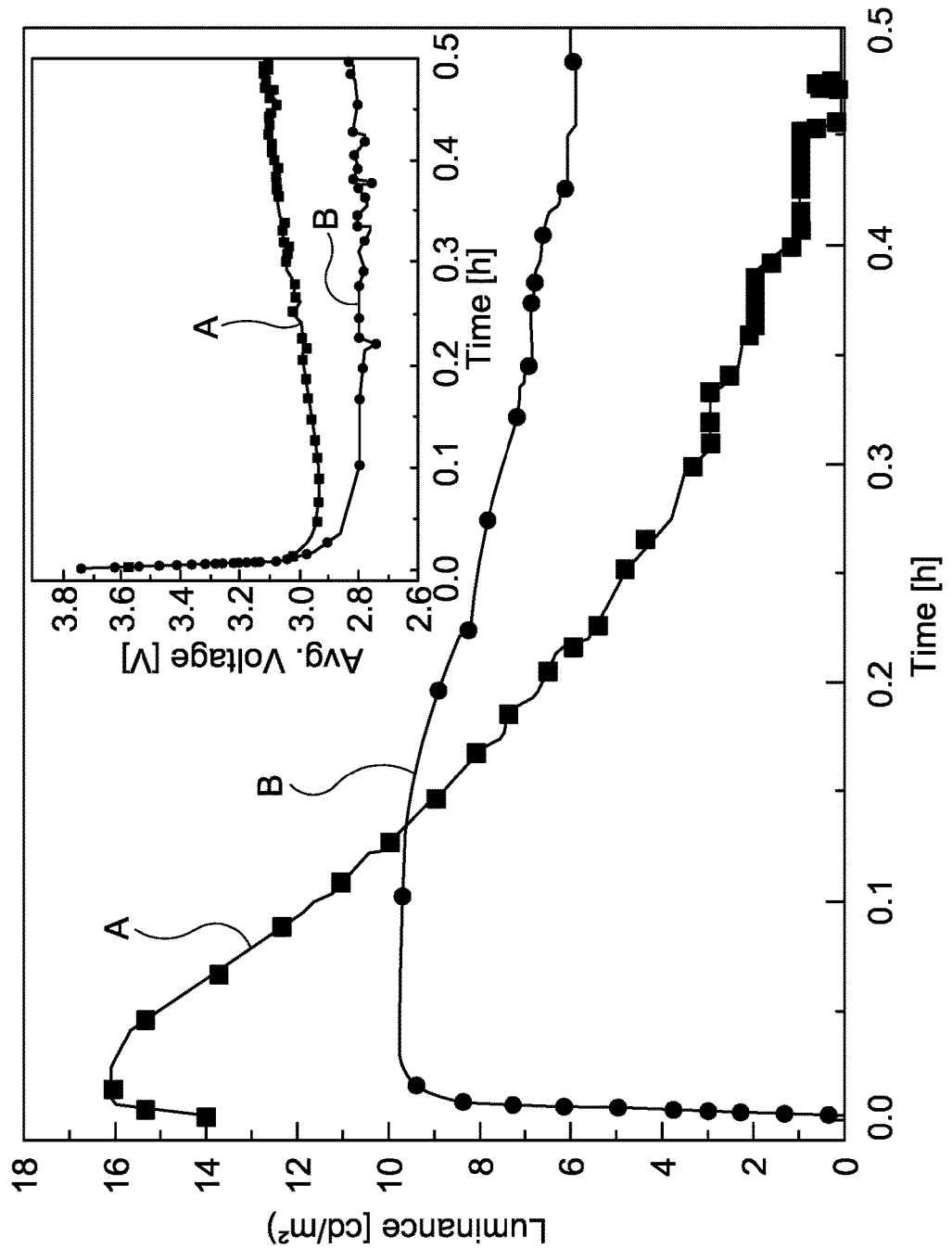
FIGS. 2a and 2b show electroluminescent behaviour of light emitting electrochemical cells.
Figure 2B:
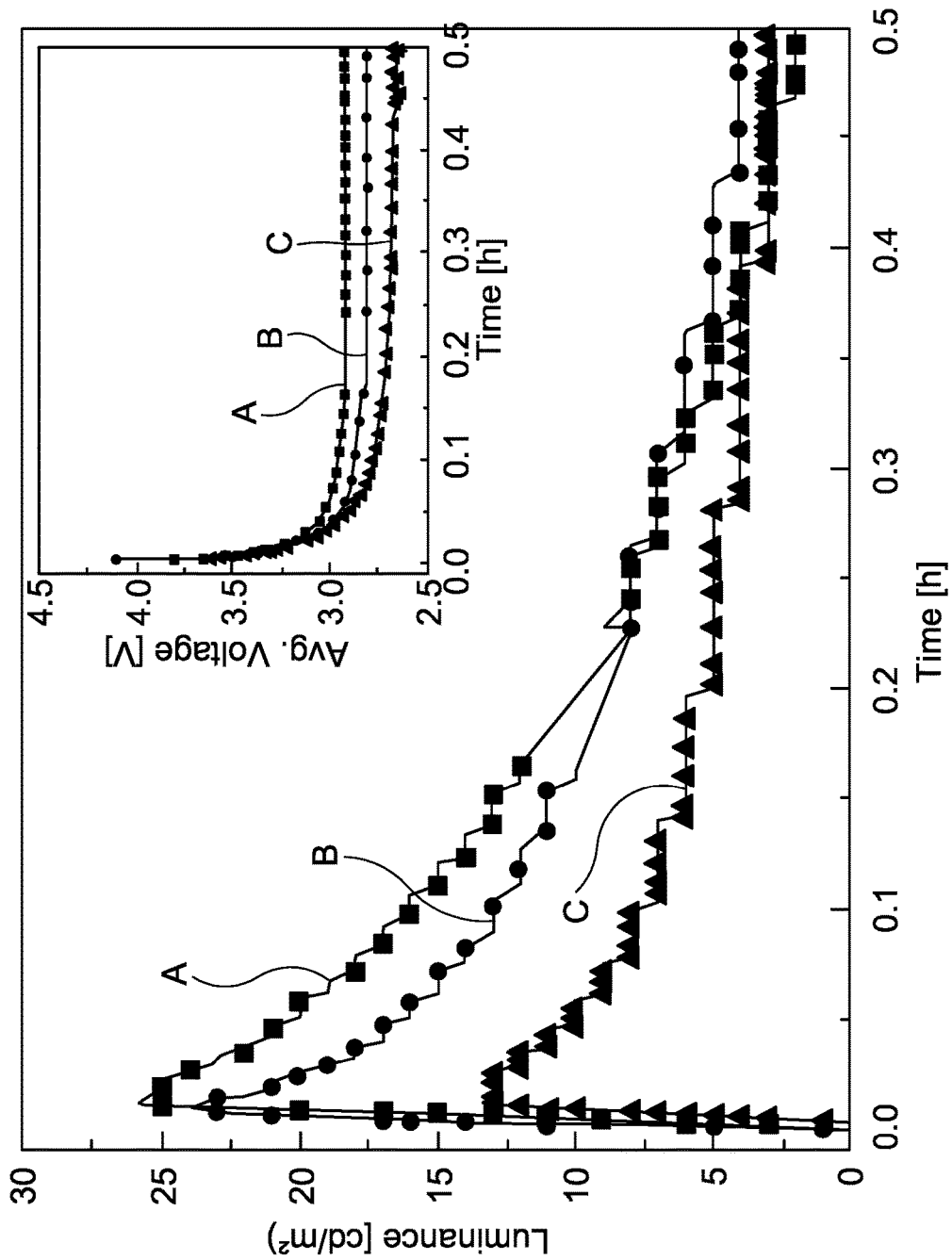

FIG. 2a shows the luminance over time of the LEEC using XII: [Bmim][PF$_6$] 4:1 mixture as the luminescent layer. The average voltage with time is shown on the insert graph. FIG. 2b shows similar graphs for the LEEC using XII only as the luminescent layer.

Different average current densities were employed as shown on FIGS. 2a and 2b:−50 Am$^{-2}$ shown as lines A, 25 Am$^{-2}$ shown as lines B and 10 Am$^{-2}$ shown as lines C The results for the different devices studied are summarized in Table 3 below. Initially, for both LEECs, the average voltage applied drops rapidly over the first seconds. Coinciding with the decrease in driving voltage, an increase in the luminance was observed. This reached a maximum value and then slowly decreased versus time.

This is typical for LEECs, as the injection barrier for electrons and holes reduces due to the migration of ions to the electrode interfaces and the subsequent formation of doped regions. The reduction of the injection barrier leads to the reduced driving voltage to sustain the set current density. With increasing operating time the doped regions expand leading to a slowly increasing quenching of the excitons, and as a result a (non-permanent) luminance reduction.

TABLE 3

Performance of LEEC devices: ITO/PEDOT:PSS/XII/Al and ITO/PEDOT:PSS/XII:[Bmim][PF$_6$] 4:1/Al biased with a block wave-pulsed current at a frecuency of 1000 Hz and a duty cycle 50% at different current densities.

| | | Electroluminescence | | | |
|---|---|---|---|---|---|
| LEEC | Avg. Current Density (A·m$^{-2}$) | Lum$_{max}$ (cd·m$^{-2}$)[a] | PCE$_{max}$ (lm·W$^{-1}$)[b] | EQE max (%)[c] | Photo-luminescence PLQY (%) |
| XII only | 10 | 13 | 0.7 | 0.39 | 16.2 |
| | 25 | 24 | 0.4 | 0.29 | |
| | 50 | 26 | 0.2 | 0.16 | |

TABLE 3-continued

Performance of LEEC devices: ITO/PEDOT:PSS/XII/Al and
ITO/PEDOT:PSS/XII:[Bmim][PF$_6$] 4:1/Al biased
with a block wave-pulsed current at a frecuency of 1000
Hz and a duty cycle 50% at different current densities.

| LEEC | Avg. Current Density (A · m$^{-2}$) | Electroluminescence | | | Photo-luminescence PLQY (%) |
|---|---|---|---|---|---|
| | | Lum$_{max}$ (cd · m$^{-2}$)$^a$ | PCE$_{max}$ (lm · W$^{-1}$)$^b$ | EQE max (%)$^c$ | |
| XII:[Bmim][PF$_6$] | 25 | 10 | 0.2 | 0.12 | 20.7 |
| | 50 | 17 | 0.1 | 0.1 | |

The table shows luminance (Lum$_{max}$), power conversion efficiency (PCE$_{max}$), external quantum efficiency (EQE$_{max}$) and photo luminescent quantum yield (PLQY) for the two LEECs tested.

In FIG. 2 it is clearly seen that the luminance decreases with decreasing current density, albeit this relationship is far from linear. A similar behaviour has been observed for ionic transition metal complex based LECs. This effect has been attributed to a reduced quenching of the excitions due to either a reduction of charge carriers, excited states or both. As the devices are operated at a fixed average current density, the efficiency of the devices is directly proportional to the luminance. With a fivefold decrease in current density, the luminance of the XII only (no ionic liquid) device drops only from approximately 26 to 13 cd m$^{-2}$. Hence, the device power efficiency strongly increases to 0.7 lum W-1 with an external quantum efficiency (EQE) of 0.39% (assuming Lambertian emission.

The electroluminescent (EL) spectra for these LEECs are similar to those of the photo luminescent spectra of FIG. 1. All cells emitted homogenously from the active area. The spectra feature an unstructured green emission centred at 538 nm (CIE coordinates: 0.35, 0.57).

REFERENCES—THE FOLLOWING
REFERENCES ARE FULLY INCORPORATED
BY REFERENCE HEREIN 1. (a) Uoyama, H.; Goushi, K.; Shizu, K.; Nomura, H.; Adachi, C. *Nature* 2012, 492, 234; (b) Nakanotani, H.; Higuchi, T.; Furukawa, T.; Masui, K.; Morimoto, K.; Numata, M.; Tanaka, H.; Sagara, Y.; Yasuda, T.; Adachi, C. Nat Commun 2014, 5, 4016; (c) Zhang, Q.; Li, J.; Shizu, K.; Huang, S.; Hirata, S.; Miyazaki, H.; Adachi, C. *J Am Chem Soc* 2012, 134, 14706; (d) Zhang, Q.; Li, B.; Huang, S.; Nomura, H.; Tanaka, H.; Adachi, C. *Nature Photonics* 2014, 8, 326.
2. Reineke, S. *Nature Photonics* 2014, 8, 269.
3. a) Lee, S. Y.; Yasuda, T.; Yang, Y. S.; Zhang, Q.; Adachi, C. *Angew Chem Int Ed Engl* 2014, 53, 6402; (b) Mehes, G.; Nomura, H.; Zhang, Q.; Nakagawa, T.; Adachi, C. *Angew Chem Int Ed Engl* 2012, 51, 11311.
4. (a) Costa, R. D.; Orti, E.; Bolink, H. J.; Monti, F.; Accorsi, G.; Armaroli, N. *Angew. Chem. Int. Ed.* 2012, 51, 8178; (b) Hu, T.; He, L.; Duan, L.; Qiu, Y. *J. Mater. Chem.* 2012, 22, 4206.
5. Pertegás, A.; Tordera, D.; Serrano-Pérez, J. J.; Orti, E.; Bolink, H. J. *J. Am. Chem. Soc.* 2013, 135, 18008.
6. Tao, Ye; et al; *Advanced Materials;* 2014, Thermally Activated delayed fluorescence materials towards the Breakthrough of Organoelectronics, 17 Sep. 2014.

The invention claimed is:
1. An electroluminescent device comprising:
a charged organic thermally activated delayed fluorescence (TADF) species; and sufficient counter ions to balance the charge on the charged organic thermally activated delayed fluorescence species, as emitter material;
wherein the emitter material comprises a compound according to formula I or formula II:

$$\text{TADF}(-Y^p)_n mA^q \qquad \qquad \text{I}$$

or $$\text{TADF}(-L-Z^p)_n mA^q \qquad \qquad \text{II}$$

wherein TADF is a metal free organic thermally activated delayed fluorescence moiety;
Y is a metal free charged species bonded to the TADF moiety;
L is a linking group; wherein each L selected from the group consisting of a substituted or unsubstituted hydrocarbylene chain, a hydrocarbylene and an unsaturated hydrocarbylene;
Z is Y bonded to L;
n is at least 1;
A is the sufficient counter ions to balance the charge;
p and q are the charges on each Y and A respectively; and
m is the number of the counter ions A, wherein p multiplied by n=m multiplied by q wherein the TADF moiety is according to formula XVI:

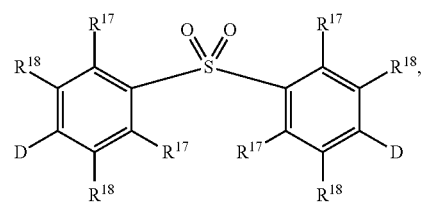

wherein each D is a donor moiety independently selected from the group consisting of:

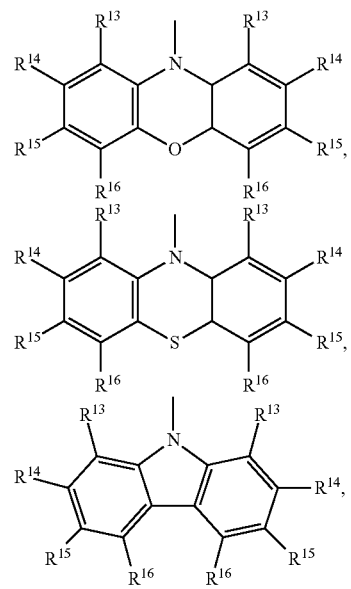

-continued

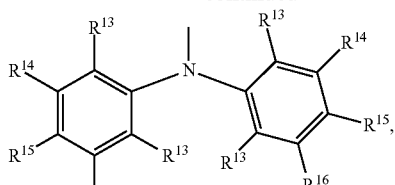

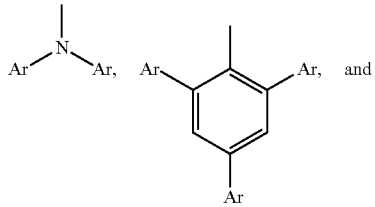

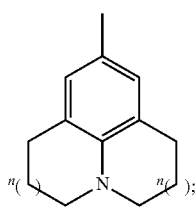

wherein;

each group $R^{11}$, $R^{12}$, $R^{13}$, $R^{14}$, $R^{15}$, $R^{16}$, $R^{17}$ and $R^{18}$ not involved in bonding to an organic charged group Z is, independently for each occurrence, selected from the group consisting of —H, substituted or unsubstituted primary, secondary or tertiary alkyl, that may be cyclic and may be unsaturated; substituted or unsubstituted aryl or heteroaryl, —CF$_3$, —OMe, —SF$_5$, —NO$_2$, halo, aryl, aryl hydroxy, amino, alkoxy, alkylthio, carboxy, cyano, thio, formyl, ester, acyl, thioacyl, amido, sulfonamido, carbamate, phosphine oxide and phosphine sulphide; and wherein groups Ar are independently for each occurrence substituted or unsubstituted aryl or heteroaryl and n ( ) indicates the optional presence of saturated —CH$_2$— groups in the rings annelated to the benzene ring, wherein n is independently for each occurrence, 0, 1, or 2 wherein Y and Z are, independently for each occurrence, selected from the group consisting of:

carboxylate, sulfonate, sulfinate, phosphonate, cyanide, thiocyanate;

quarternary amine groups of forms 1, 2, 3, 4:

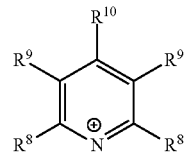

1

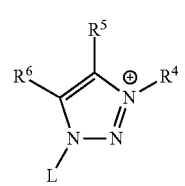

2

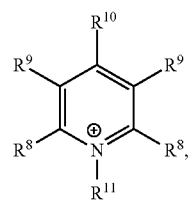

3

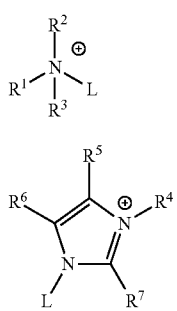

4 wherein -L indicates the position of bonding to the linking group L or directly to the TADF moiety; $R^1$, $R^2$, $R^3$, $R^4$, $R^5$, $R^6$, $R^7$, $R^8$, $R^9$ and $R^{10}$ are, independently for each occurrence, selected from the group consisting of —H, substituted or unsubstituted primary, secondary or tertiary alkyl, that may be cyclic and may be unsaturated; substituted or unsubstituted aryl or heteroaryl, —CF$_3$, —OMe, —SF$_5$, —NO$_2$, halo, aryl, aryl hydroxy, amino, alkoxy, alkylthio, carboxy, cyano, thio, formyl, ester, acyl, thioacyl, amido, sulfonamido, and carbamate;

quarternary amine group of form 5:

5

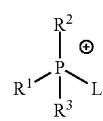

wherein one of $R^8$, $R^9$, $R^{10}$ and $R^{11}$ bonds to the linking group L or directly to the TADF moiety and the others of $R^8$, $R^9$, $R^{10}$ and $R^{11}$, independently for each occurrence selected from the group consisting of —H, substituted or unsubstituted primary, secondary or tertiary alkyl, that may be cyclic and may be unsaturated; substituted or unsubstituted aryl or heteroaryl, —CF$_3$, —OMe, —SF$_5$, —NO$_2$, halo, aryl, aryl hydroxy, amino, alkoxy, alkylthio, carboxy, cyano, thio, formyl, ester, acyl, thioacyl, amido, sulfonamido, and carbamate;

and quaternary phosphorus groups of the form 6:

6 wherein $R^1$, $R^2$ and $R^3$ are, independently for each occurrence, selected from the group consisting of —H, substituted or unsubstituted primary, secondary or tertiary alkyl, that may be cyclic and may be unsaturated;

substituted or unsubstituted aryl or heteroaryl, —CF$_3$, —OMe, —SF$_5$, —NO$_2$, halo, aryl, aryl hydroxy, amino, alkoxy, alkylthio, carboxy, cyano, thio, formyl, ester, acyl, thioacyl, amido, sulfonamido, and carbamate, wherein -L indicates the position of bonding to the linking group L or directly to the TADF moiety.

2. The electroluminescent device of claim 1, selected from the group consisting of:

a light-emitting electrochemical cell (LEEC); and an organic light emitting diode (OLED).

3. The electroluminescent device of claim 1, wherein the compound of formula II includes one linking group L, that consists of a hydrocarbylene chain, for each group Z.

4. The electroluminescent device of claim 1, wherein linking groups L are unsubstituted hydrocarbylene chains of the form:

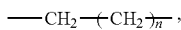

wherein n is from 0 to 10 or even 0 to 5 and the hydrocarbylene chain optionally contains one or more unsaturations.

5. The electroluminescent device of claim 1, wherein the linking group L is selected from the group consisting of cyclopentane-1,3-diyl; cyclohexane-1,4-diyl; 1,4-phenylene; and 4,4'-biphenylene.

6. The electroluminescent device of claim 1, wherein the compounds of formula II take the form of formula III or formula IV:

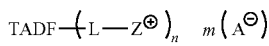     III

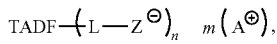     IV wherein n is at least 1 and n=m.

7. The electroluminescent device of claim 1, wherein the quarternary amine groups are:

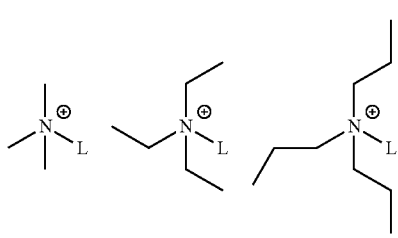

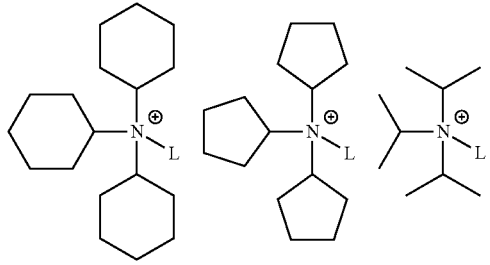

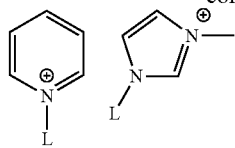

wherein -L indicates the position of bonding to the linking group L or directly to the TADF moiety.

8. The electroluminescent device of claim 1, wherein the quaternary phosphorus groups selected from the group consisting of:

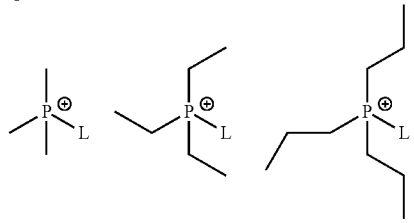

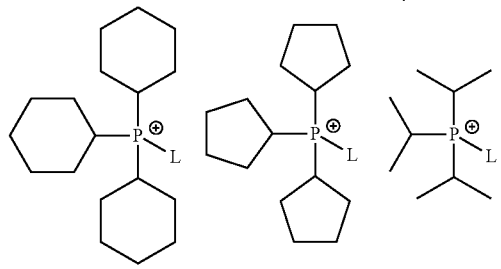

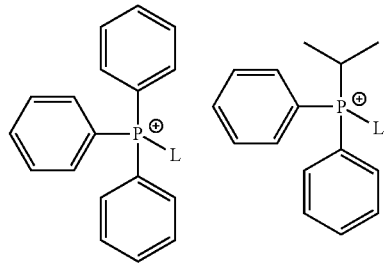

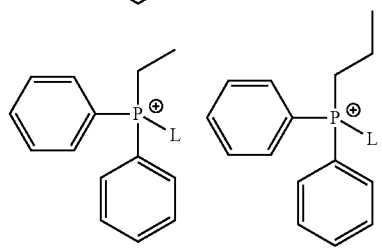

wherein -L indicates the position of bonding to the linking group L or directly to the TADF moiety.

9. The electroluminescent device of claim 1, wherein the donor D is:

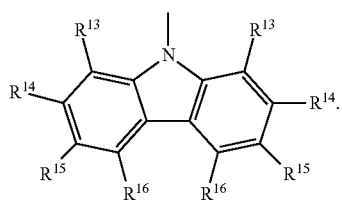

10. The electroluminescent device of claim 1, wherein the metal free charged organic thermally activated delayed fluorescence species is according to formula XVIa or XVIb XVIa

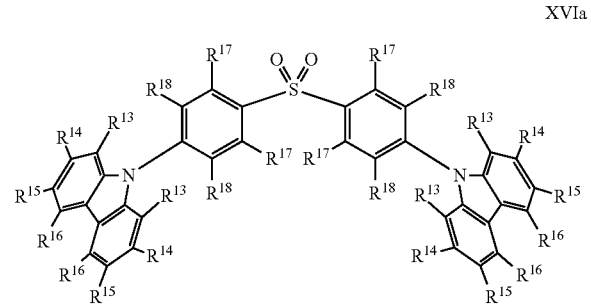

-continued

XVIb

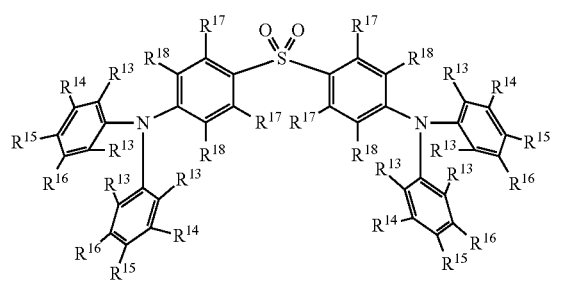

wherein at least one of the occurrences of $R^{13}$, $R^{14}$, $R^{15}$, $R^{16}$, $R^{17}$ and $R^{18}$ represents the bonding position, either directly or via the linking group L, to the charged group Z, each L if present and each Z having, independently for each occurrence, the same meanings as for compounds of formula III or IV; and wherein each group of $R^{13}$, $R^{14}$, $R^{15}$, $R^{16}$, $R^{17}$ and $R^{18}$ not involved in bonding to the charged group Z is, independently for each occurrence, selected from the group consisting of —H, substituted or unsubstituted primary, secondary or tertiary alkyl, that may be cyclic and may be unsaturated; substituted or unsubstituted aryl or heteroaryl, —CF$_3$, —OMe, —SF$_5$, —NO$_2$, halo, aryl, aryl hydroxy, amino, alkoxy, alkylthio, carboxy, cyano, thio, formyl, ester, acyl, thioacyl, amido, sulfonamido, phosphine oxide, phosphine sulphide and carbamate.

11. The electroluminescent device of claim 10, wherein the metal free charged organic thermally activated delayed fluorescence species is according to formula XVIc or formula XVId XVIc

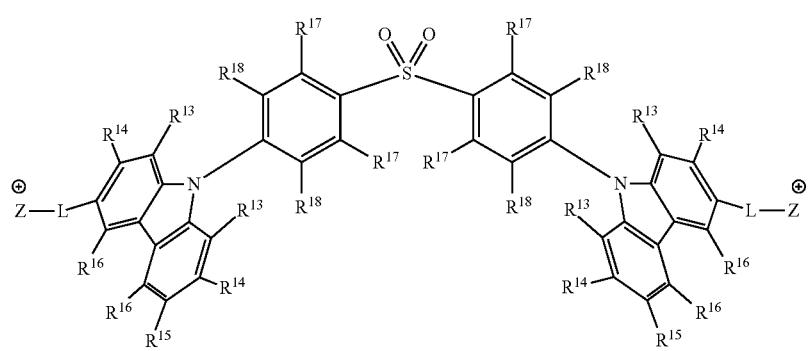

XVId

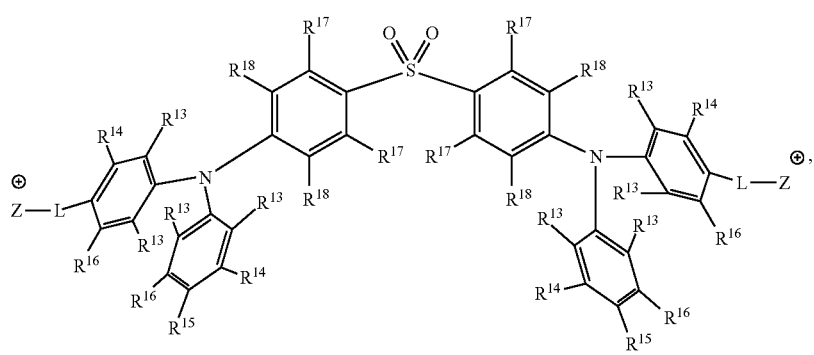

wherein the groups $R^{13}$, $R^{14}$, $R^{15}$, $R^{16}$, $R^{17}$, $R^{18}$ and Z take the same meaning as in claim 10, except $R^{15}$ is not involved in bonding to Z; linking group L may be present or absent.

12. The electroluminescent device of claim 11, wherein the metal free charged organic thermally activated delayed fluorescence species is according to one of formulas of formulas XVIe and XVIf:

XVIe

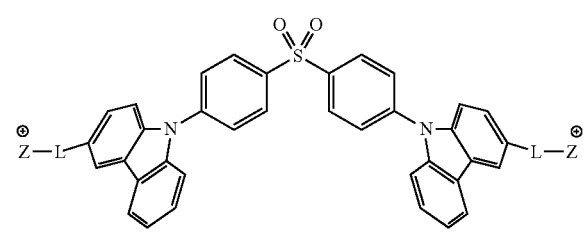

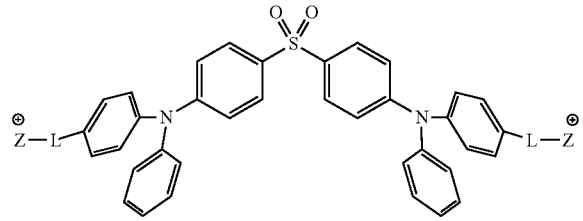

XVIf wherein for each occurrence L is absent or is independently selected from the group consisting of:

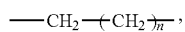

wherein n is from 0 to 10;

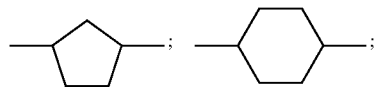

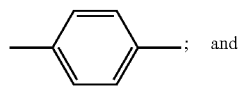; and

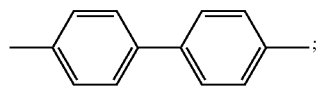;

wherein for each occurrence Z is independently selected from the group consisting of:

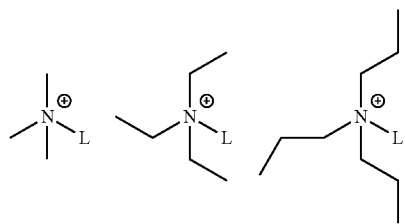

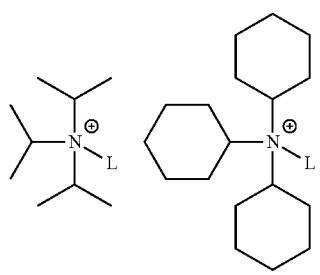

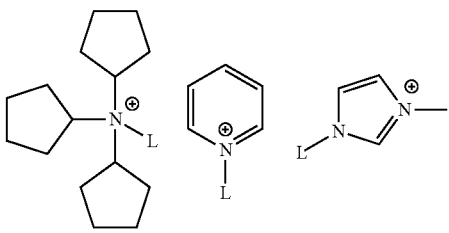

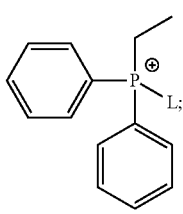

wherein -L indicates the position of bonding to linking group L or directly to the carbazole ring if L is absent.

13. The electroluminescent device of claim 1, wherein the emitter material comprises a compound of any one of formulas XVII and XX:

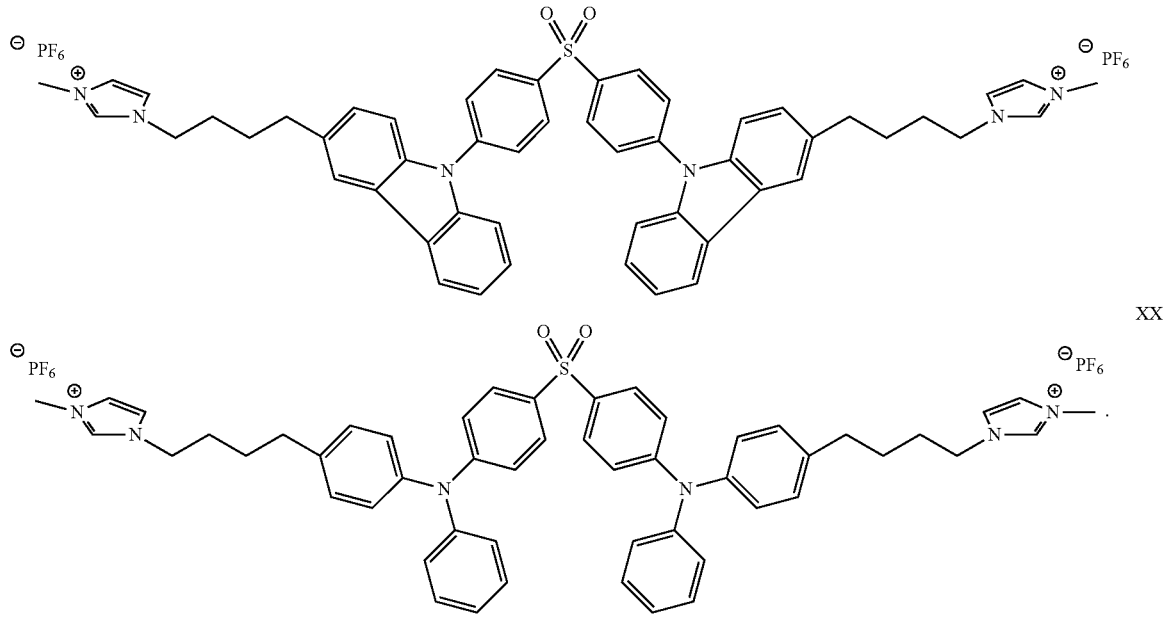

14. The electroluminescent device of claim 1, wherein the charged organic thermally activated delayed fluorescence species is charged by a substituent or substituents that is/are an integral part of the TADF species.

15. The electroluminescent device of claim 1, wherein A is selected from the group consisting of: halide, $PF_6^-$, $BF_4^-$, $BR_4^-$; wherein R is an aryl group, selected from phenyl; $OTf^-$, $OTs^-$, $SbX_6^-$ wherein X is halide, $NTf_2^- NO_3^-$, $CO_3^{2-}$; cations of first and second group elements in the periodic table and quaternary ammonium cations.

16. The electroluminescent device of claim 1, wherein the emitter material is provided in a luminescent layer that comprises an ionic liquid.

17. A method of producing light, the method comprising:
manufacturing an electroluminescent device including a metal free charged organic thermally activated delayed fluorescence (TADF) charged organic species or mixtures thereof; and sufficient counter ions to balance the charge on the charged organic TADF species, or mixtures thereof as emitter material; and
operating the electroluminescent device under conditions capable of producing light;
wherein the metal charged organic thermally activated delayed fluorescence species and counter ions are as defined in claim 1.

* * * * *